(12) United States Patent
Castanon et al.

(10) Patent No.: US 10,765,815 B2
(45) Date of Patent: Sep. 8, 2020

(54) RETRACTABLE NEEDLE SYRINGE

(71) Applicant: L.O.M. LABORATORIES INC., Vancouver (CA)

(72) Inventors: Scott E. Castanon, Carlsbad, CA (US); Ralph E. Woloschuk, St. Albert (CA); Warren Marc Terry, San Diego, CA (US)

(73) Assignee: L.O.M. Laboratories Inc., Vancouver, CA (US)

(*) Notice: Subject to any disclaimer, the term of this patent is extended or adjusted under 35 U.S.C. 154(b) by 656 days.

(21) Appl. No.: 15/521,858

(22) PCT Filed: Oct. 30, 2015

(86) PCT No.: PCT/CA2015/051113
§ 371 (c)(1),
(2) Date: Apr. 25, 2017

(87) PCT Pub. No.: WO2016/065484
PCT Pub. Date: May 6, 2016

(65) Prior Publication Data
US 2017/0239425 A1    Aug. 24, 2017

Related U.S. Application Data

(60) Provisional application No. 62/105,624, filed on Jan. 20, 2015, provisional application No. 62/073,748, filed on Oct. 31, 2014.

(51) Int. Cl.
*A61M 5/32* (2006.01)
*A61M 5/20* (2006.01)
*A61M 5/50* (2006.01)

(52) U.S. Cl.
CPC ........ *A61M 5/3234* (2013.01); *A61M 5/2046* (2013.01); *A61M 5/3221* (2013.01);
(Continued)

(58) Field of Classification Search
CPC .. A61M 5/3232; A61M 5/322; A61M 5/3234; A61M 5/3293; A61M 5/508;
(Continued)

(56) References Cited

U.S. PATENT DOCUMENTS 4,978,340 A    12/1990   Terrill
5,098,390 A     3/1992   Wallingford
(Continued)

FOREIGN PATENT DOCUMENTS

CA    2291660 A1    11/1998
CA    2332918 A1    12/1999
(Continued)

OTHER PUBLICATIONS

Maxxon Applauds New Federal Needlestick Act Press Release, Nov. 2, 2000, Business Wire.
(Continued)

*Primary Examiner* — Manuel A Mendez
*Assistant Examiner* — Tasnim Mehjabin Ahmed
(74) *Attorney, Agent, or Firm* — Oyen Wiggs Green & Mutala LLP

(57) ABSTRACT

A pneumatically activated retractable-needle syringe comprising a syringe barrel, a plunger, a needle, a needle hub, a locking tip, a propellant gas release cell and a rupture mechanism is provided. The plunger has a retraction lumen defined therein for receiving the needle when the retractable-needle syringe is actuated.

19 Claims, 18 Drawing Sheets

(52) U.S. Cl.
CPC ........... *A61M 5/3293* (2013.01); *A61M 5/502* (2013.01); *A61M 5/508* (2013.01); *A61M 2005/3231* (2013.01); *A61M 2005/3242* (2013.01)

(58) Field of Classification Search
CPC .. A61M 2005/3241; A61M 2005/3236; A61M 2005/3235; A61M 2005/3239; A61M 2005/3231; A61M 2005/3242; A61M 2005/3123
See application file for complete search history.

(56) References Cited

U.S. PATENT DOCUMENTS

| | | | |
|---|---|---|---|
| 5,118,614 A | 6/1992 | Rybak | |
| 5,120,310 A | 6/1992 | Shaw | |
| 5,122,118 A | 6/1992 | Haber | |
| 5,125,898 A * | 6/1992 | Kaufhold, Jr. | A61M 5/3234 604/110 |
| 5,176,640 A | 1/1993 | Nacci | |
| 5,188,614 A | 2/1993 | Hart | |
| 5,211,628 A | 5/1993 | Marshall | |
| 5,224,936 A | 7/1993 | Gallagher | |
| 5,279,580 A | 1/1994 | Wallingford | |
| 5,334,155 A | 8/1994 | Sobel | |
| 5,360,404 A | 11/1994 | Novacek | |
| 5,389,076 A | 2/1995 | Shaw | |
| 5,407,436 A | 4/1995 | Toft | |
| 5,423,758 A | 6/1995 | Shaw | |
| 5,433,712 A | 7/1995 | Stiles | |
| 5,533,970 A | 7/1996 | Berger | |
| 5,575,777 A | 11/1996 | Cover | |
| 5,578,011 A | 11/1996 | Shaw | |
| 5,632,733 A | 5/1997 | Shaw | |
| 5,702,367 A | 12/1997 | Cover | |
| 5,716,341 A | 2/1998 | Saito | |
| 5,779,679 A | 7/1998 | Shaw | |
| 5,797,880 A | 8/1998 | Erskine | |
| 5,810,775 A | 9/1998 | Shaw | |
| 5,845,957 A | 12/1998 | Hurst | |
| 5,868,713 A | 2/1999 | Klippenstein | |
| 5,882,342 A | 3/1999 | Cooper | |
| 5,935,104 A | 8/1999 | Janek | |
| 5,989,220 A | 11/1999 | Shaw | |
| 5,997,512 A | 12/1999 | Shaw | |
| 6,015,438 A | 1/2000 | Shaw | |
| 6,077,245 A * | 6/2000 | Heinrich | A61M 5/3234 604/110 |
| 6,083,199 A | 7/2000 | Thorley | |
| 6,086,568 A | 7/2000 | Caizza | |
| 6,090,077 A * | 7/2000 | Shaw | A61M 5/3234 604/110 |
| 6,099,500 A | 8/2000 | Dysarz | |
| 6,179,812 B1 | 1/2001 | Botich | |
| 6,183,440 B1 | 2/2001 | Bell | |
| 6,193,695 B1 | 2/2001 | Rippstein | |
| 6,206,853 B1 | 3/2001 | Bonnet | |
| 6,210,371 B1 | 4/2001 | Shaw | |
| 6,221,055 B1 | 4/2001 | Shaw | |
| 6,241,707 B1 | 6/2001 | Dysarz | |
| 6,267,749 B1 | 7/2001 | Miklos | |
| 6,361,525 B2 | 3/2002 | Capes | |
| 6,406,461 B1 | 6/2002 | Ellingsen | |
| 6,409,701 B1 | 6/2002 | Cohn | |
| 6,413,236 B1 | 7/2002 | Van Dyke | |
| 6,413,237 B1 | 7/2002 | Caizza | |
| 6,432,087 B1 | 8/2002 | Hoeck | |
| 6,458,105 B1 | 10/2002 | Rippstein | |
| 6,474,472 B1 | 11/2002 | Shaw | |
| 6,494,863 B1 | 12/2002 | Shaw | |
| 6,558,357 B1 | 5/2003 | Hoeck | |
| 6,572,565 B2 | 6/2003 | Daley | |
| 6,572,584 B1 | 6/2003 | Shaw | |
| 6,585,690 B1 | 7/2003 | Hoeck | |
| 6,599,268 B1 | 7/2003 | Townsend | |
| 6,679,863 B2 | 1/2004 | Bush | |
| 6,692,470 B2 | 2/2004 | Sanpietro | |
| 6,740,062 B2 | 5/2004 | Hjertman | |
| 6,767,335 B1 | 7/2004 | Helg | |
| 6,846,301 B2 | 1/2005 | Smith | |
| 6,868,713 B2 | 3/2005 | Bolz | |
| 6,872,193 B2 | 3/2005 | Shaw | |
| RE39,107 E | 5/2006 | Shaw | |
| 7,090,656 B1 | 8/2006 | Botich | |
| 7,182,734 B2 | 2/2007 | Saulenas | |
| 7,258,678 B2 | 8/2007 | Wilkinson | |
| 7,294,118 B2 | 11/2007 | Saulenas | |
| 7,303,547 B2 | 12/2007 | Pressly, Sr. | |
| 7,344,517 B2 | 3/2008 | Schiller | |
| 7,351,224 B1 | 4/2008 | Shaw | |
| D617,453 S | 6/2010 | Shaw | |
| D617,454 S | 6/2010 | Shaw | |
| 7,740,615 B2 | 6/2010 | Shaw | |
| 7,803,132 B2 * | 9/2010 | Janek | A61M 5/3234 604/110 |
| 7,811,259 B2 | 10/2010 | Klippenstein | |
| 7,846,135 B2 | 12/2010 | Runfola | |
| D645,962 S | 9/2011 | Shaw | |
| 8,048,031 B2 | 11/2011 | Shaw | |
| D660,420 S | 5/2012 | Shaw | |
| 8,167,848 B2 | 5/2012 | Klippenstein | |
| 8,469,927 B2 | 6/2013 | Shaw | |
| 8,496,600 B2 | 7/2013 | Shaw | |
| 8,523,810 B2 | 9/2013 | Klippenstein | |
| 8,535,267 B2 | 9/2013 | Caizza | |
| 8,574,193 B2 | 11/2013 | Caizza | |
| 8,758,296 B2 | 6/2014 | Woehr et al. | |
| 8,777,504 B2 | 7/2014 | Shaw | |
| 9,138,545 B2 | 9/2015 | Shaw | |
| 9,192,732 B2 | 11/2015 | Klippenstein | |
| 9,408,983 B2 | 8/2016 | Klippenstein | |
| 9,649,450 B2 | 5/2017 | Klippenstein | |
| 10,195,364 B2 * | 2/2019 | Andersen | A61M 5/3234 |
| 2003/0004491 A1 | 1/2003 | Tenhuisen | |
| 2003/0040717 A1 | 2/2003 | Saulenas | |
| 2003/0078540 A1 | 4/2003 | Saulenas | |
| 2003/0176843 A1 | 9/2003 | Wilkinson | |
| 2004/0153034 A1 | 8/2004 | Fan | |
| 2005/0159705 A1 | 7/2005 | Crawford | |
| 2005/0159707 A1 | 7/2005 | Schiller | |
| 2005/0215951 A1 | 9/2005 | Saulenas | |
| 2006/0084919 A1 | 4/2006 | Shaw | |
| 2006/0111671 A1 * | 5/2006 | Klippenstein | A61M 5/31591 604/110 |
| 2007/0260189 A1 | 11/2007 | Shaw | |
| 2008/0119786 A1 | 5/2008 | Stewart | |
| 2008/0132851 A1 | 6/2008 | Shaw | |
| 2008/0208122 A1 | 8/2008 | Walton | |
| 2008/0221517 A1 | 9/2008 | Shaw | |
| 2009/0306601 A1 | 12/2009 | Shaw | |
| 2010/0000040 A1 | 1/2010 | Shaw | |
| 2010/0125252 A1 * | 5/2010 | Tseng | A61M 5/3234 604/195 |
| 2010/0222739 A1 | 9/2010 | Klippenstein | |
| 2011/0021989 A1 | 1/2011 | Janek | |
| 2011/0064512 A1 | 3/2011 | Shaw | |
| 2011/0125097 A1 | 5/2011 | Shaw | |
| 2011/0213304 A1 | 9/2011 | Schraga | |
| 2011/0230844 A1 | 9/2011 | Shaw | |
| 2012/0004621 A1 | 1/2012 | Shaw | |
| 2012/0184903 A1 | 7/2012 | Klippenstein | |
| 2012/0259243 A1 | 10/2012 | Shaw | |
| 2012/0323181 A1 | 12/2012 | Shaw | |
| 2013/0261551 A1 | 10/2013 | Shaw | |
| 2013/0345632 A1 | 12/2013 | Klippenstein | |
| 2014/0012206 A1 | 1/2014 | Shaw | |
| 2014/0171876 A1 | 6/2014 | Shaw | |
| 2014/0171877 A1 | 6/2014 | Shaw | |
| 2014/0276435 A1 | 9/2014 | Shaw | |
| 2014/0276445 A1 | 9/2014 | Shaw | |
| 2015/0073303 A1 | 3/2015 | Shaw | |

(56) References Cited

U.S. PATENT DOCUMENTS

| | | | |
|---|---|---|---|
| 2015/0283329 A1 | 10/2015 | Shaw | |
| 2016/0045676 A1 | 2/2016 | Klippenstein | |
| 2017/0100548 A1 | 4/2017 | Andersen | |

FOREIGN PATENT DOCUMENTS

| | | |
|---|---|---|
| CA | 2437415 A1 | 2/2002 |
| CA | 2455160 A1 | 6/2004 |
| CA | 2495571 A1 | 6/2004 |
| CA | 2548722 A1 | 6/2005 |
| CA | 2651037 A1 | 11/2007 |
| CA | 2713152 A1 | 8/2009 |
| CA | 2724197 A1 | 12/2009 |
| CA | 2728548 A1 | 1/2010 |
| CA | 2744433 A1 | 6/2010 |
| CA | 2758026 A1 | 11/2010 |
| CA | 2785561 A1 | 8/2011 |
| CA | 2802547 A1 | 1/2012 |
| CA | 2809510 A1 | 2/2012 |
| CA | 2818325 A1 | 5/2012 |
| CN | 2853080 Y | 1/2007 |
| CN | 101193675 A | 4/2008 |
| CN | 102247635 A | 11/2011 |
| EP | 479217 A1 | 4/1992 |
| EP | 596211 A1 | 5/1994 |
| FR | 2831448 A1 | 5/2003 |
| JP | 6142204 A | 5/1994 |
| NL | 9000292 A | 9/1991 |
| WO | 91/04760 A1 | 4/1991 |
| WO | 9205818 | 4/1992 |
| WO | 93/018810 A1 | 9/1993 |
| WO | 95/01811 A1 | 1/1995 |
| WO | 96/35463 A1 | 11/1996 |
| WO | 98/34659 A1 | 8/1998 |
| WO | 99/25401 A1 | 5/1999 |
| WO | 00/02607 A1 | 1/2000 |
| WO | 00/057940 A1 | 10/2000 |
| WO | 00/061061 A2 | 10/2000 |
| WO | 01/024852 A1 | 4/2001 |
| WO | 01/080930 A1 | 11/2001 |
| WO | 02/011796 A1 | 2/2002 |
| WO | 03/051435 A1 | 6/2003 |
| WO | 2004/050138 A2 | 6/2004 |
| WO | 2004/060451 A1 | 7/2004 |
| WO | 2004/082747 A1 | 9/2004 |
| WO | 2005/011792 A1 | 2/2005 |
| WO | 2005/058399 A1 | 6/2005 |
| WO | 2005/070292 A1 | 8/2005 |
| WO | 2005/072801 A1 | 8/2005 |
| WO | 2006/017889 A1 | 2/2006 |
| WO | 2006/024172 A1 | 3/2006 |
| WO | 2006/044010 A2 | 4/2006 |
| WO | 2006/108243 A2 | 10/2006 |
| WO | 2006/119570 A1 | 11/2006 |
| WO | 2007/131086 A2 | 11/2007 |
| WO | 2009/102624 A1 | 8/2009 |
| WO | 2009/151704 A1 | 12/2009 |
| WO | 2010/002757 A1 | 1/2010 |
| WO | 2010/065375 A1 | 6/2010 |
| WO | 2010/132196 A1 | 11/2010 |
| WO | 2011/066022 A1 | 6/2011 |
| WO | 2011/100039 A1 | 8/2011 |
| WO | 2012/003343 A1 | 1/2012 |
| WO | 2012/015644 A1 | 2/2012 |
| WO | 2012/067778 A1 | 5/2012 |
| WO | 2012/162821 A1 | 12/2012 |
| WO | 2012/174109 A1 | 12/2012 |
| WO | 2013/126819 A1 | 8/2013 |
| WO | 2014/093026 A1 | 6/2014 |
| WO | 2014/143220 A1 | 9/2014 |
| WO | 2014/143221 A1 | 9/2014 |
| WO | 2015/034548 A1 | 3/2015 |
| WO | 2015/034549 A1 | 3/2015 |
| WO | 2015/080724 A1 | 6/2015 |
| WO | 2015145207 A1 | 10/2015 |
| WO | 2016/115628 A1 | 7/2016 |

OTHER PUBLICATIONS

Maxxon Safety Syringe Press Release, Feb. 2000, online: <http://www.micro-stocks.com/Research/MXON.htm>.

Maxxon Announces Safety Syringe Patent Filing, Advance for Respiratory Care Practitioner, Daily News Watch, Feb. 2000, online:<http://www.advanceforrcp.com/previousdnw/rcdnwjan31.html>.

\* cited by examiner

RETRACTABLE NEEDLE SYRINGE

CROSS-REFERENCE TO RELATED APPLICATIONS

This application is a 371 of Patent Cooperation Treaty patent application No. PCT/CA2015/051113 filed 30 Oct. 2015, which claims priority to, and the benefit of, United States provisional patent application Nos. 62/073,748 filed 31 Oct. 2014 and 62/105,624 filed 20 Jan. 2015. All of the foregoing applications are incorporated by reference herein in their entirety for all purposes.

TECHNICAL FIELD

Some embodiments of the present invention relate to a syringe having a retractable needle. In some embodiments, the syringe is a pneumatically-actuated retractable-needle syringe.

BACKGROUND

It is well known that many dangerous communicable diseases are spread through contacting the body fluids of an infected person. After use of a syringe, residual body fluids are likely to remain on or within the syringe needle. For this reason, syringes are typically intended for a single use only. In order to be handled safely after use, the needle of a syringe must be covered to prevent it from accidentally stabbing a person who is, for example, collecting the syringe for disposal, thereby releasing residual body fluids into such person. Typically, a protective cap is provided with the syringe, which after use of the syringe can be used to cover the tip of the needle. However, it sometimes happens that persons attempting to cap a used needle miss the cap and accidentally stab themselves, resulting in potential exposure to communicable diseases.

Accordingly, it is desirable to provide a syringe wherein the needle can be retracted into the syringe following use. Syringes including retractable needles wherein the retraction of the needle is accomplished by means of pneumatic actuation have been developed, as exemplified by U.S. Pat. No. 5,868,713 to Klippenstein and U.S. Pat. No. 7,811,259 to Klippenstein, both of which are incorporated by reference herein.

The foregoing examples of the related art and limitations related thereto are intended to be illustrative and not exclusive. Other limitations of the related art will become apparent to those of skill in the art upon a reading of the specification and a study of the drawings.

SUMMARY

In one aspect, a retractable-needle syringe is provided. The syringe has a syringe barrel, a plunger slidably disposed within and sealingly engaged with the syringe barrel, the plunger having a retraction lumen define therein for receiving a needle when the retractable-needle syringe is actuated, a needle coupled to a distal end of the syringe barrel and in fluid communication with a medicament chamber defined within the syringe barrel distally of the plunger, a needle hub for securing the needle at the distal end of the syringe barrel, the needle hub being initially secured within a false wall against a loading force or an injection force applied by a user, and releasable from the false wall in response to a post-injection force applied by a user, a locking tip provided at a distal end of the plunger, the locking tip being in sealing engagement with and initially secured within the retraction lumen against a loading force or an injection force applied by a user, and releasable for sliding retraction within the plunger lumen in response to release of propellant upon a post-injection force applied by a user, the locking tip being engageable with the needle hub in response to the post-injection force to provide a retraction assembly comprising the locking tip, the needle header, and the needle, a propellant release cell positioned distally of the needle hub and containing a propellant, and a rupture mechanism positioned to puncture the propellant release cell in response to the application of the post-injection force by a user to thereby drive retraction of the retraction assembly within the retraction lumen.

In another aspect, a retractable-needle syringe has a barrel, a plunger axially slideable within the barrel for drawing medicament into a medicament chamber defined within the barrel and for injecting medicament into a patient, the plunger having a retraction lumen therein, a locking tip engaged at a distal end of the plunger within the retraction lumen, a false wall initially engaged within the barrel near a distal end of the barrel, the false wall being moveable in a distal direction in response to application of a post-injection force by a user, a needle hub initially secured by the false wall, the needle hub being engageable with the locking tip to provide a retraction assembly comprising the locking tip, the needle header, and the needle, and the needle hub being releasable from the false wall upon the application of the post-injection force by the user, a needle projecting from the distal end of the barrel, the needle being secured to the needle hub, a unitary propellant release structure provided distally of the needle hub within the barrel, and a rupturing member moveable to rupture the unitary propellant release structure upon the application of the post-injection force by the user to thereby drive retraction of the retraction assembly within the retraction lumen.

In some aspects, the needle hub has barbs and the locking tip is made of a relatively softer material than the barbs, so that the barbs can be engaged with the locking tip upon the application of the post-injection force by the user to provide the retraction assembly.

BRIEF DESCRIPTION OF DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

In this specification, "seals" or "sealingly engages" means that two elements are engaged with sufficient sealing capability that the function for which the sealing is provided can be effectively performed.

"Distal" means the direction towards the tip of the needle when the syringe assembly is in the assembled state. "Proximal" means the direction opposite of distal, i.e. the direction away from the tip of the needle when the syringe assembly is in the assembled state.

"Downstream" means a direction in the distal direction, i.e. towards the tip of the needle, referring to the conventional direction of injection of medicament into a patient. "Upstream" means a direction opposite to downstream, i.e. in the proximal direction, e.g. in the direction of fluid flow when medicament is being drawn from a supply vial into the syringe for subsequent injection.

"Inwardly" means in a direction towards the axial centerline of the syringe. "Outwardly" means in a direction towards the outside of the syringe, i.e. away from the axial centerline of the syringe.

"Injection force" means a force that would typically be applied by a user to the plunger of a syringe to inject a medicament into a patient.

"Post-injection force" means a force that is applied to activate the propellant-actuated retraction mechanism described below after a user has completed injection of the medicament. In some embodiments, the post-injection force is greater than the injection force.

"Loading force" means a force typically applied by a user when drawing medicament into a syringe in preparation for administering that medicament to a patient.

Figure 1:
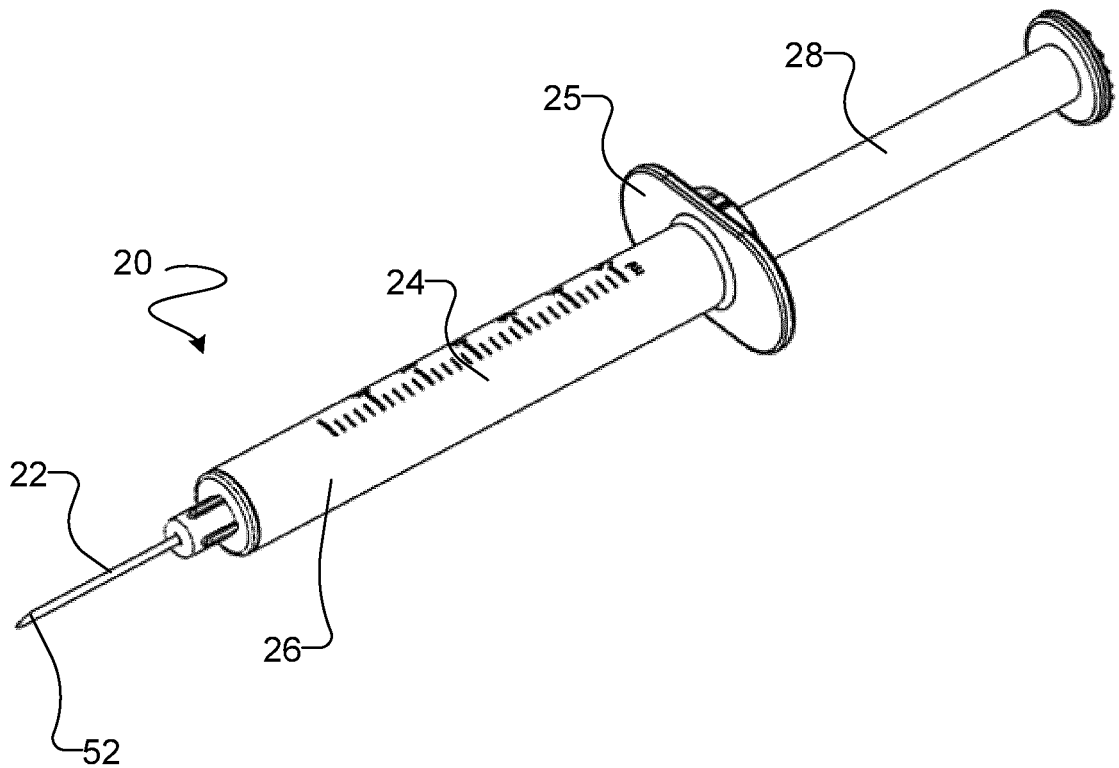
FIG. 1 is a perspective view of an example embodiment of a retractable needle syringe.

With reference to FIG. 1, in one embodiment of a retractable needle syringe, a hypodermic needle 22 is coupled to a syringe 24 for use in administration of a medicament to a patient using a plunger 28. Syringe 24 has a barrel 26, a plunger 28 slidingly and sealingly engageable within the barrel 26, and a retractable needle 22 at its distal tip. The overall assembly of syringe 24, plunger 28 and needle 22 provides a syringe assembly 20. In the illustrated embodiment, the syringe 24 has a volume of 3 mL, with graduated volume markings provided on the barrel 26 of syringe 24, but syringes having any desired volume can be made and gradated volume markings are an optional feature that is present in some embodiments.

Figure 2:
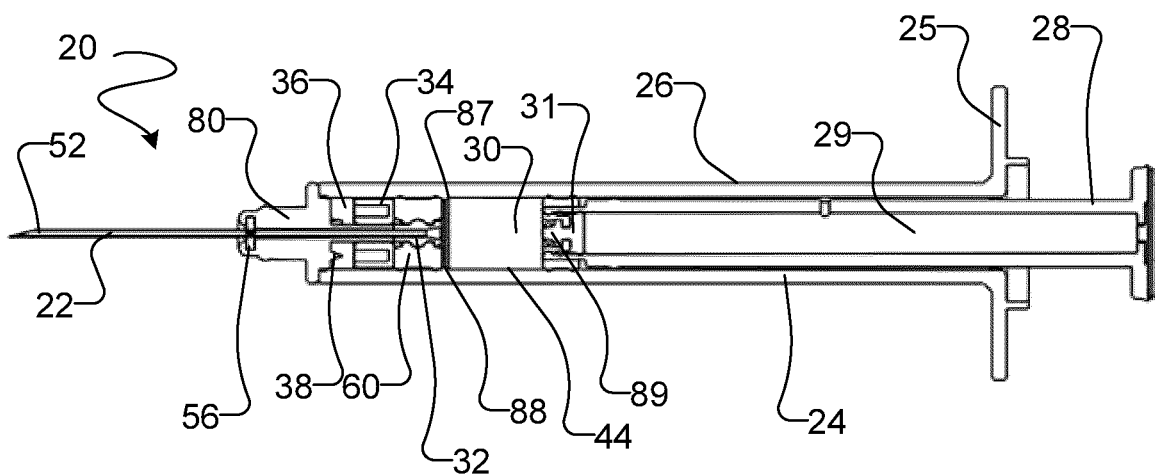
FIG. 2 is a cross-sectional view of the embodiment illustrated in FIG. 1.

With reference to FIG. 2, a medicament chamber 30 is defined between retractable needle 22, the distal end of plunger 28 and an interior surface 44 of syringe barrel 26 for containing the medicament to be administered to the subject. Medicament chamber 30 is in fluid communication with needle 22 when syringe assembly 20 is in the assembled configuration, and plunger 28 is sealingly and slideably engaged within barrel 26 to move fluid within medicament chamber 30 through needle 22.

Syringe 24 preferably includes a flange 25 formed therewith or attached thereto to facilitate grasping and usage of syringe assembly 20 by a user. In some embodiments, flange 25 is provided at or near the proximal end of syringe 24. Flange 25 may be any suitable shape and configuration to facilitate use of syringe assembly 20 by a user, for example a generally circular or oval extension projecting radially outwardly from the barrel 26 of syringe 24 or a pair of opposed projecting tabs serving as finger grips to facilitate manipulation of syringe 24 relative to plunger 28 by a user.

Needle 22 projects from the distal end of syringe 24, and the hollow interior of needle 22 is in fluid communication with medicament chamber 30 so that medicament can be delivered into a patient. Needle 22 is securely retained by a needle hub 32 and false wall 60 so that needle 22 is securely retained in place when syringe assembly 20 is in normal use, i.e. during loading of medicament into medicament chamber 30 and during injection of medicament into a subject. Needle 22 is releasable (via release of needle header 32 as described below) in response to force applied by the puncture of propellant release cell 34 so that needle 22 can be retracted into the body of syringe 24 upon the application of a post-injection force by a user, as described below.

In some embodiments, a cap 50 (FIG. 4) is provided to cover needle 22 prior to use. Cap 50 may be laminated, cemented, snapped, press fit, or otherwise affixed to needle guide 80 (described below) to secure it in place prior to use. In alternative embodiments, cap 50 is secured to the distal portion of syringe barrel 26. Cap 50 can be snapped off or otherwise removed in any suitable manner to expose needle 22 for use. In some embodiments, cap 50 includes radially outwardly projecting, longitudinally extending ridges 55 or other surface features to facilitate removal of cap 50. In some embodiments, a plurality of alignment and/or snap features can be provided to engage cap 50 with the distal end of syringe 24 and/or with needle guide 80, as described below.

Figure 3:
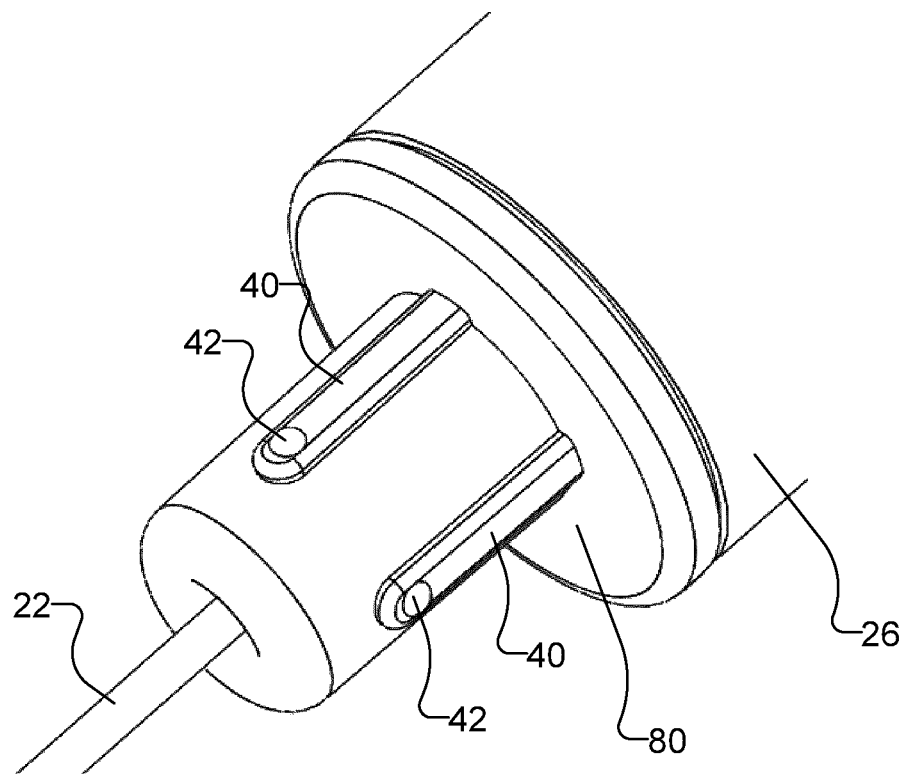
FIG. 3 is a perspective view showing alignment tabs on an example embodiment of a needle guide.
Figure 4:
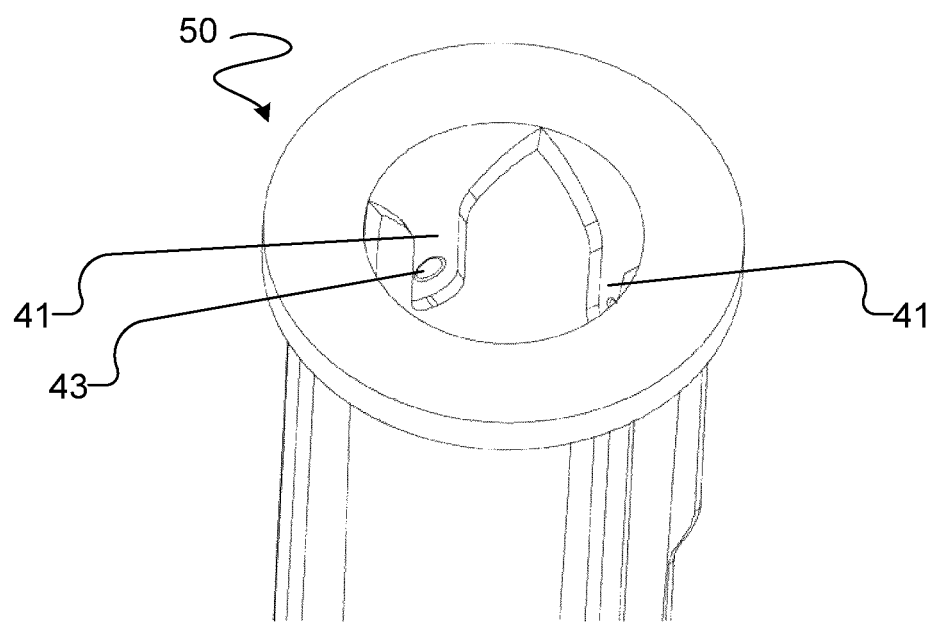
FIG. 4 is a perspective view showing recessed channels formed in an example embodiment of a needle cap.

In the illustrated embodiment with reference to FIGS. 3 and 4, to secure cap 50 to syringe 24, a plurality of radially outwardly projecting alignment tabs 40 are provided on the outside circumference of the distal portion of needle guide 80, and are positioned and configured to align with corresponding recessed channels 41 formed at the proximal end of the inside surface of cap 50. The sliding engagement of alignment tabs 40 and recessed channels 41 guides cap 50 to the secured position. To secure cap 50 in the secured position, the illustrated embodiment also includes a plurality of radially outwardly extending snap projections 42 (positioned one on each of the alignment tabs 40 in the illustrated embodiment), that are engageable with a plurality of corresponding snap depressions 43 formed on the inside of cap 50. The described example embodiment is just one way that cap 50 can be secured to syringe 24 to cover needle 22, and any suitable needle cover can be used for this purpose.

To provide pneumatic force to retract needle 22 and with reference to FIG. 2, a propellant release cell 34 is provided within syringe barrel 26 within a propellant release chamber 36, and a puncture mechanism such as puncture lances 38 for puncturing propellant release cell 34 upon application of a post-injection force by a user is provided. In some embodiments, puncture lances 38 are provided within propellant release chamber 36. The release of propellant from propellant release cell 34 into propellant release chamber 36 applies a force against the needle retraction assembly 108 described below, to retract needle 22 into retraction lumen 29 defined within plunger 28.

Figure 5:
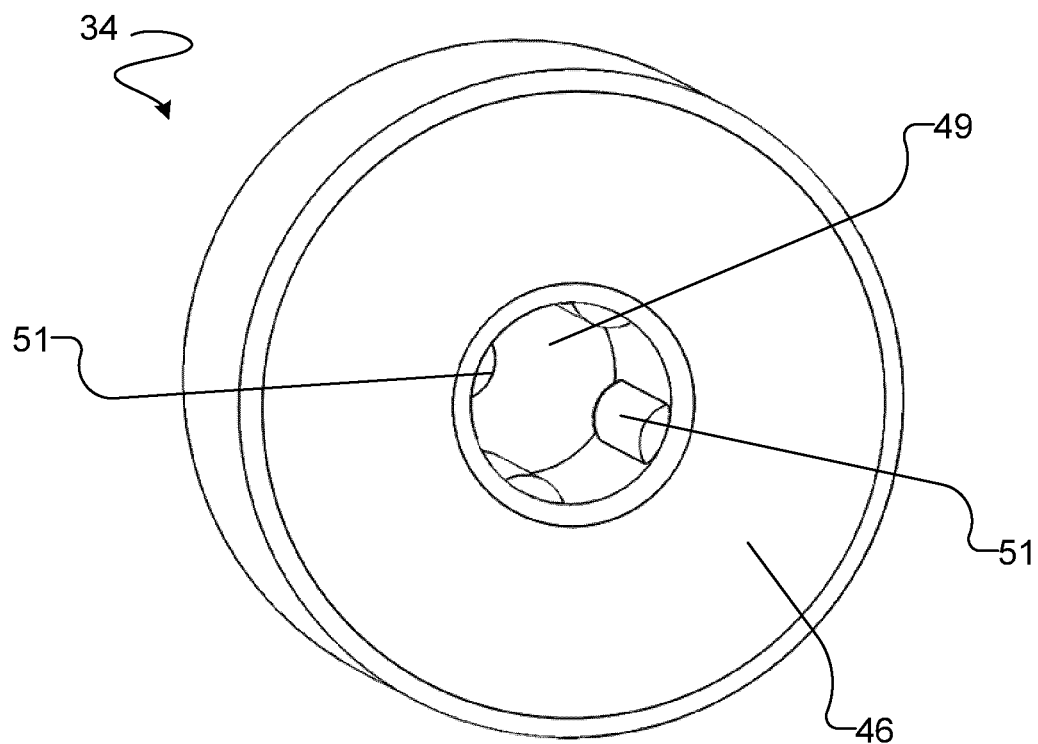
FIG. 5 shows an example embodiment of a propellant release cell.
Figure 6:
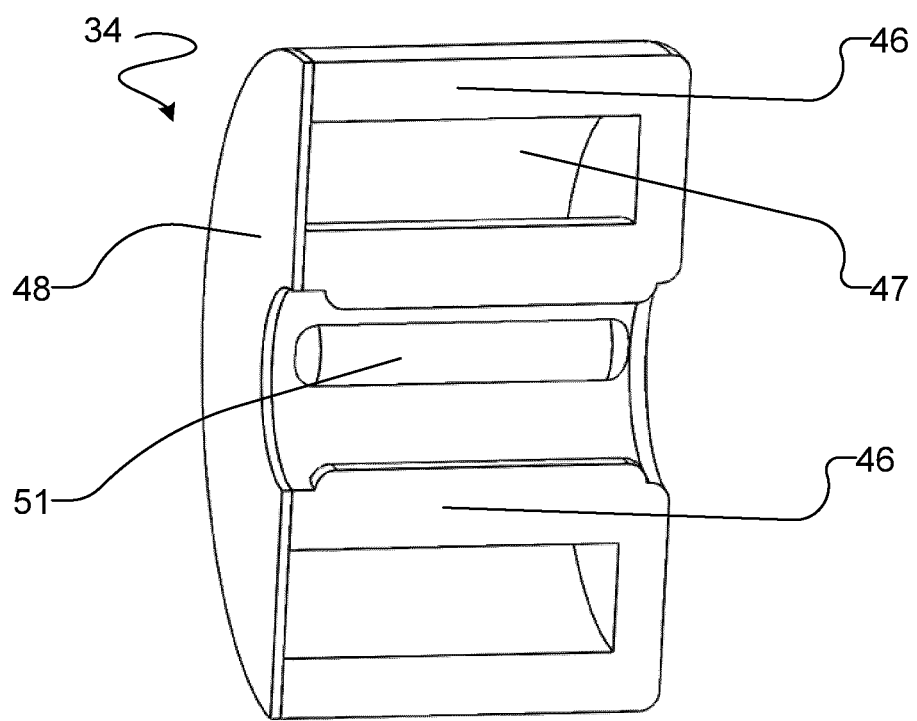
FIG. 6 shows a cross-sectional view of the example embodiment of a propellant release cell depicted in FIG. 5.

In the illustrated embodiment, with particular reference to FIGS. 5 and 6, an example embodiment of a propellant release cell 34 has a rigid outer shell 46 defining a propellant chamber 47 therein. Propellant is retained within propellant chamber 47 in an enclosure that contains the propellant. In the illustrated embodiment, the propellant is retained by the sealing engagement of a sealing membrane 48 engaged with an upper lip of rigid outer shell 46. Examples of propellant release cells 34 that can be used in some embodiments of the present invention include gas release cells such as are described in Patent Cooperation Treaty patent application No. PCT/IB2014/060187 filed 26 Mar. 2014 and entitled Gas Release Cell, which is incorporated by reference herein in its entirety. In other embodiments, other types of propellant release cells or enclosures containing propellant may be used, two substances that can be mixed together to produce a gas can be contained within propellant release cell 34, or the like.

In the illustrated embodiment, propellant release cell 34 has an axially extending central aperture 49, so that the overall shape of propellant release cell 34 is cylindrical with an axially extending aperture 49 therethrough to allow needle 22 to pass through propellant release cell 34. In the illustrated embodiment, the interior circumference of propellant release cell 34 has been provided with a plurality of axially extending ribs 51 that project radially inwardly. In some embodiments, ribs 51 help to ensure that a passageway for propellant flow remains available at all times, so that when propellant contained in propellant release cell 34 is released, there is a passageway through which propellant can travel to reach the needle retraction assembly 108 as described below. In the illustrated embodiment, a central aperture 49 of propellant release cell 34 encircles elongate central neck 84 (FIG. 10) of needle guide 80, and ribs 51 help to prevent formation of a seal between the interior circumference of propellant release cell 34 and elongate central neck 84 after propellant release cell 34 has been punctured. In embodiments with other configurations, ribs 51 could help to prevent formation of a seal between propellant release cell 34 and other components of syringe assembly 20. In some embodiments, ribs 51 are omitted and the tolerance between propellant release cell 34 and other components of syringe assembly 20 such as elongate central neck 84 is sufficient to ensure that a passageway for enabling the flow of released propellant remains available after propellant release cell 34 has been punctured.

With reference to FIG. 2, to facilitate retraction of needle 22 upon release of propellant from propellant release cell 34, plunger 28 includes a retraction lumen 29 defined therewithin for receiving needle 22 when needle 22 is retracted and a locking tip 31 at a distal end of plunger 28 for assisting in the retraction of needle 22 by engaging with a needle hub 32 to provide a needle retraction assembly 108 in the manner described below.

Figure 7:
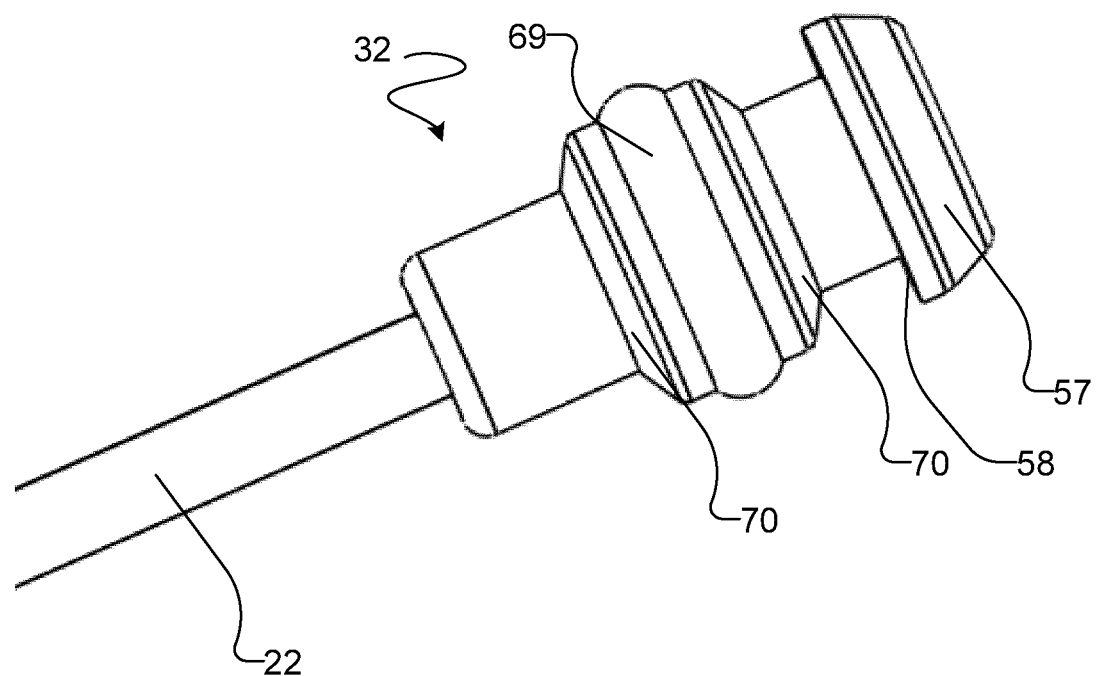
FIG. 7 is a perspective view of a needle hub according to an example embodiment.

With particular reference to FIG. 7, in the illustrated embodiment, needle 22 is releasably retained in its initial position via needle hub 32, as described below. Needle hub 32 is provided at or near the proximal end of needle 22. In some embodiments, needle 22 may be crimped in, cemented to, or otherwise securely fixed to needle hub 32. In some embodiments, needle 22 is insert molded with needle hub 32 to create a single part. Needle hub 32 securely retains needle 22 in place against the distally applied injection force of medicament being injected into a patient or against a proximal loading force when medicament is drawn into medicament chamber 30, but is releasable in the proximal direction in response to a post-injection force applied by a user, as described below.

Needle hub 32 includes snap features for engaging with locking tip 31 provided on plunger 28 to yield needle retraction assembly 108, sealing features for providing a sealing engagement with locking tip 31 so that fluid cannot pass through needle 22 after locking tip 31 has engaged with needle hub 32, and engagement features for initially sealingly securing needle hub 32 in false wall 60. The engagement features allow release of needle hub 32 from false wall 60 in response to the application of a post-injection force by a user.

Figure 11A:
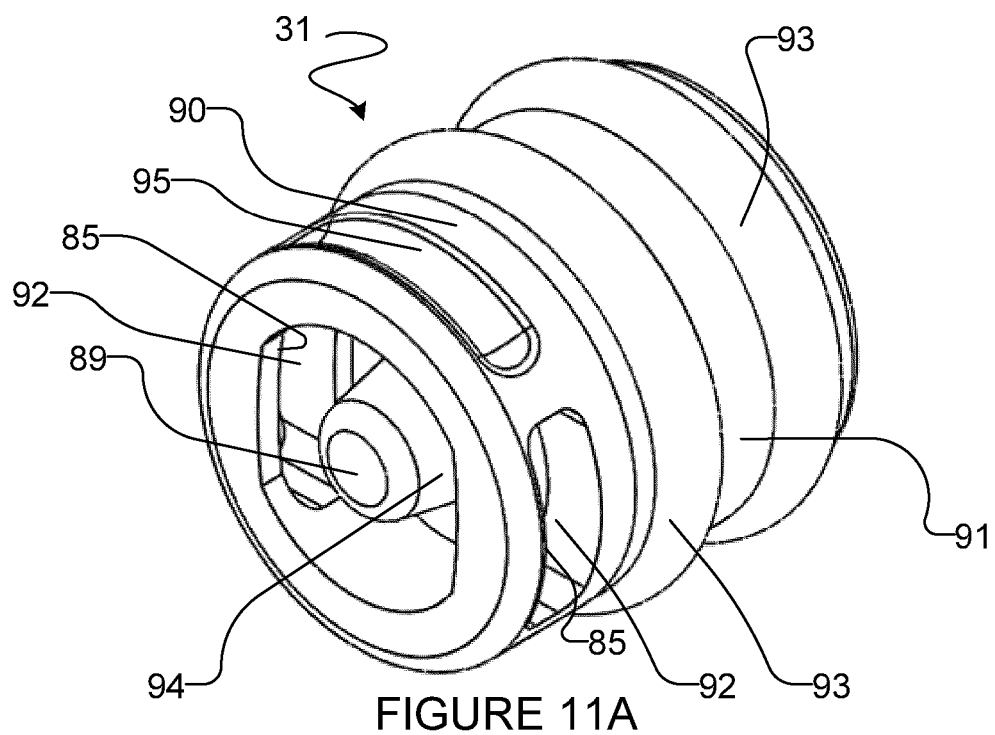
FIG. 11A is a perspective view of a locking tip according to one example embodiment.

In the illustrated embodiment, the snap features of needle hub 32 comprise a generally cylindrical locking element at the proximal end of the needle hub that is positioned to engage with a locking channel 92 and locking edge 85 (FIG. 11A) provided on locking tip 31 when a user applies a post-injection force to syringe 20. The generally cylindrical locking element of needle hub 32 has a tapered portion 57, and a generally flat locking edge 58. Tapered portion 57 flares radially outwardly in the distal direction on the proximal end of needle hub 32, to provide locking edge 58 of needle hub 32 along the outside distal edge of portion thereof. In use, tapered portion 57 can slide inside locking tip 31 of plunger 28, to allow locking edge 58 to slide past and engage with locking channel 92 and locking edge 85 of plunger locking tip 31 as described below.

Although the locking element has been described and exemplified as generally cylindrical, it is alternatively possible for the locking element to be provided as one or more discrete projections positioned to be engageable by locking channel 92 in use (i.e. the generally cylindrical locking element could be broken into one or more discontinuous pieces, rather than being one fully revolved element). In some embodiments, providing the locking element of needle hub 32 as a generally cylindrical locking element eliminates a need to ensure that needle hub 32 is placed in a specific orientation during the manufacture of syringe assembly 20 (i.e. so that the locking element will be available for engagement with locking channel 92 no matter what orientation it is inserted at within false wall 60).

In some embodiments, the amount of force required to engage the needle hub 32 with the locking tip 31 is very low, for example less than 1 lb of force. In some embodiments, providing one structural feature for engaging needle hub 32 with locking tip 31 (i.e. locking edges 58 and 85 in the illustrated embodiment) and a separate structural feature for providing a seal between needle hub 32 and locking tip 31 (i.e. tapered surfaces 64 and 94, described below) allows for better refinement of the force required to sealingly engage needle hub 32 and locking tip 31.

Figure 8:
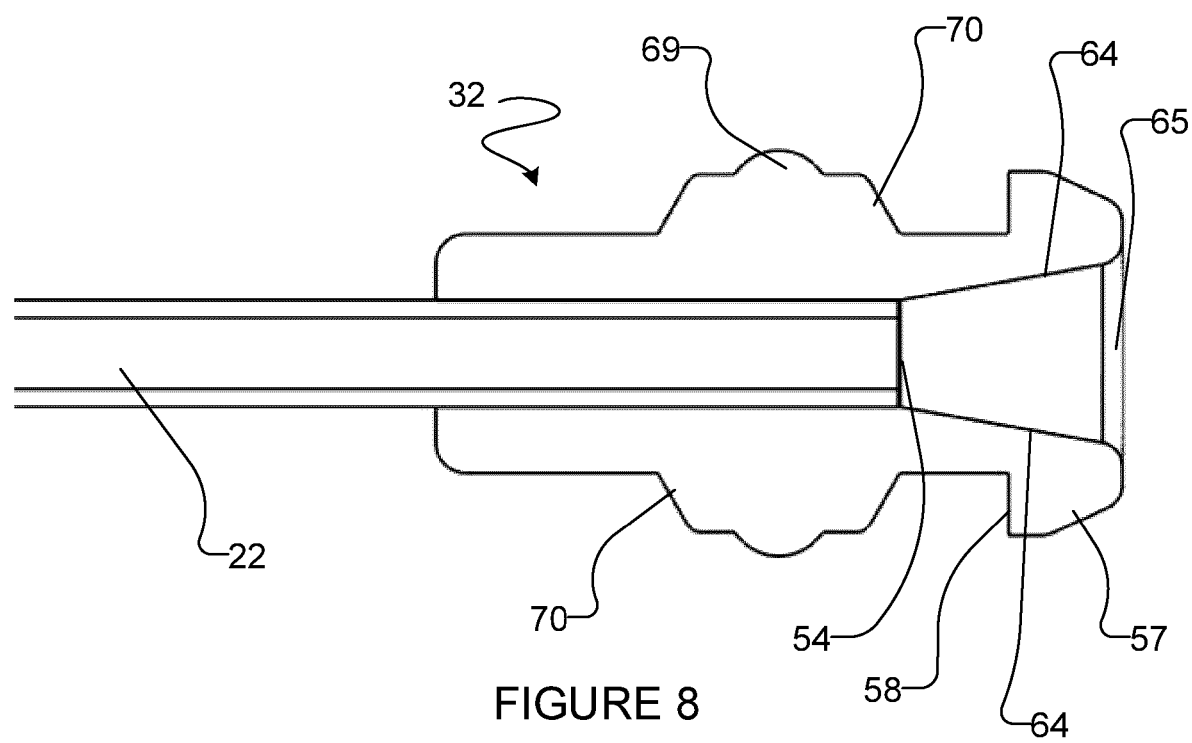
FIG. 8 is a cross-sectional view of the needle hub depicted in FIG. 7.

In the illustrated embodiment, with reference to FIG. 8, the sealing features of needle hub 32 that sealingly engaged with locking tip 31 comprise a tapered surface 64 that engages with a correspondingly tapered surface 94 on central projection 89 of locking tip 31. In the illustrated embodiment, tapered surface 64 is provided in the proximal portion of needle hub 32, which is generally cylindrical with an axially extending opening 65 therethrough, so that fluid can flow through needle 22 into and out of medicament chamber 30. Tapered surface 64 tapers inwardly in the distal direction, so that tapered surface 64 tapers inwardly towards the proximal portion of needle 22. The proximal portion of opening 65 is thus wider than the distal portion of opening 65, so that tapered surface 94 of locking tip 31 can be received therein.

Figure 9A:
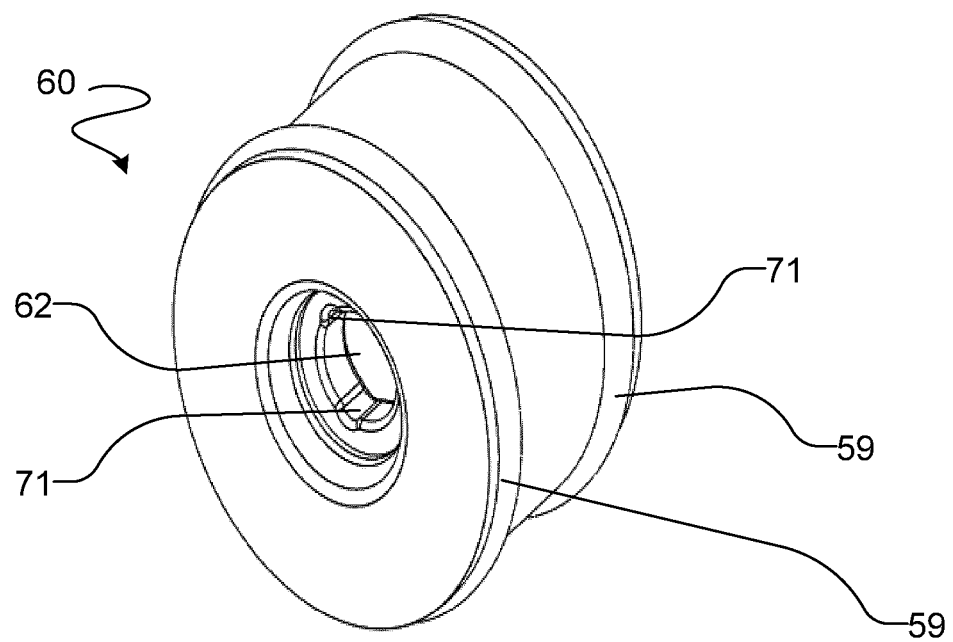
FIG. 9A is a perspective view of a false wall according to an example embodiment.
Figure 9B:
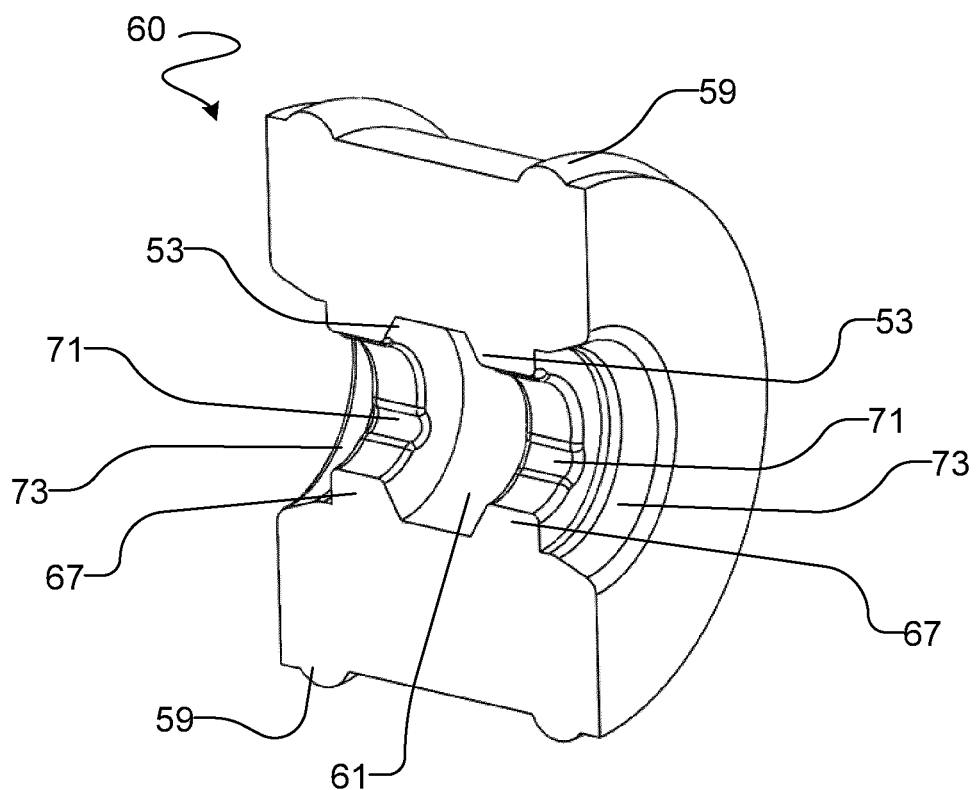
FIG. 9B is a cross-sectional view of a false wall according to an example embodiment.

In the illustrated embodiment, the engagement features of needle hub 32 that engage with false wall 60 to hold needle hub 32 (and thus needle 22) in place are an O-ring seal 69 and two tapered seals 70. O-ring seal 69 and tapered seals 70 are generally cylindrical in shape. The engagement features are provided on needle hub 32 distally of the locking element, so that the locking element of hub 32 is available to engage with locking tip 31 in use. In the illustrated embodiment, O-ring seal 69 is provided as a sealing rib integrally formed with needle hub 32. The O-ring seal 69 provided by the sealing rib sealingly engages with recess 61 of false wall 60 (FIG. 9B). The tapered seals 70 of hub 32 engage respectively with correspondingly shaped tapered regions 53 of false wall 60 to provide an additional seal to prevent medicament from flowing between needle hub 32 and false wall 60. All of false wall 60, O-ring seal 69 and tapered seals 70 are concentric, so that O-ring seal 69 and tapered seals 70 sealingly engage about their full circumferences with recess 61 of false wall 60.

Needle hub 32 is secured in place within syringe barrel 26 by engagement with false wall 60. False wall 60 is a generally cylindrical element dimensioned to fit securely within syringe barrel 26. False wall 60 is frictionally but slidably engaged with the interior surface 44 of syringe barrel 26. False wall 60 is axially slidable within barrel 26 in response to the application of a post-injection force, but is retained in place within barrel 26 during the application of an injection force. False wall 60 is also retained in place within barrel 26 during the application of a force in the proximal direction required to load medicament into medicament chamber 30 (i.e. a loading force). False wall 60 could be secured in place in any suitable manner that is sufficiently strong to retain false wall 60 in place during the application of an injection or loading force, but releasable in response to the application of a post-injection force. For example, false wall 60 could be initially held in place by breakable tabs or weakly secured with an adhesive. In the illustrated embodiment, false wall 60 assists in puncturing propellant release cell 34 in response to the application of a post-injection force, as described below.

In the illustrated embodiment, a false wall retention feature 88 in the form of a syringe interior wall (FIG. 2) that extends around the circumference of the inner surface 44 of syringe barrel 26 and projects radially inwardly is provided to facilitate positioning of false wall 60 during the assembly of syringe assembly 20. False wall retention feature 88 is a radially inwardly extending projection on the interior surface 44 of syringe barrel 26. False wall retention feature 88 is located axially along syringe barrel 26 at an appropriate position so that false wall 60 can be inserted inside syringe barrel 26 through its distal opening and contact false wall retention feature 88 at a point where false wall 60 will be contacted by the distal tip of plunger 28 at or near the end of the application of an injection force by a user. Thus, false wall retention feature 88 defines the axial location of false wall 60 during assembly.

Figure 9C:
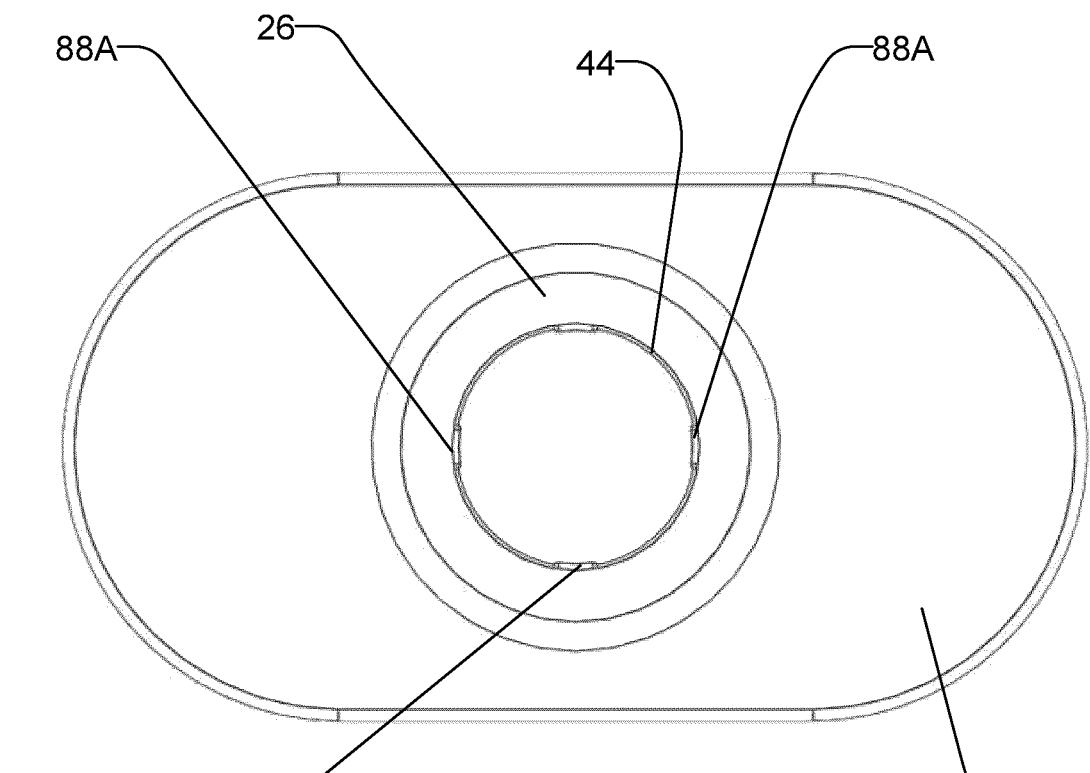
FIG. 9C is an end view of an example embodiment of a syringe barrel showing the configuration of an example embodiment of a false wall retaining feature.

In some embodiments, as illustrated in FIG. 9C, the false wall retention feature is provided as one or more discrete projections 88A that extend radially inwardly from interior surface 44 of syringe barrel 26, rather than being provided as a fully revolved feature. In the illustrated embodiment of FIG. 9C, four projections 88A are provided that extend radially inwardly, to prevent false wall 60 from being inserted too far in the proximal direction within syringe barrel 26 during assembly. While projections 88A have been illustrated as being four in number and symmetrically disposed about the interior circumference of syringe barrel 26, any number and position of projections 88A could be used (e.g. two, three, five, six, seven, eight, nine, ten, or more), so long as these projections 88A are sufficient to prevent false wall 60 (and therefore needle hub 32 and needle 22, which are supported and positioned by false wall 60) from sliding too far in the proximal direction.

Figure 10:
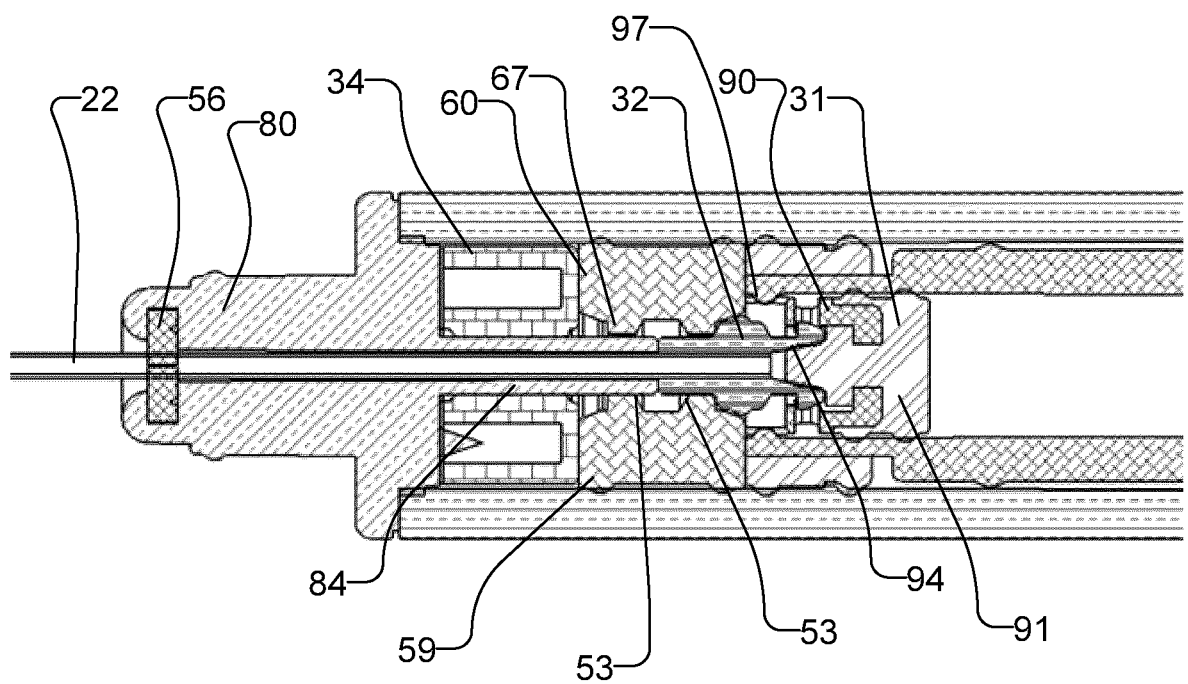
FIG. 10 is a partial cross-sectional view showing the components of an example embodiment.

False wall 60 has a central aperture 62 (FIG. 9A) therethrough for receiving needle hub 32. With reference to FIGS. 9A, 9B and 10, in the illustrated embodiment, false wall 60 includes a pair of radially outwardly projecting o-ring features 59 on its outer surface. In some embodiments, o-ring features 59 help to ensure a good seal between false wall 60 and the interior surface 44 of syringe barrel 26. O-ring features 59 can also help to ensure reproducible movement of false wall 60 within syringe barrel 26 when the user applies a post-injection force as described below, for example by ensuring consistent sliding of false wall 60 in the axial direction and maintaining an appropriate axial alignment of false wall 60 within syringe barrel 26.

False wall 60 also includes a recess 73 for receiving the locking element of needle hub 32, i.e. tapered portion 57 and locking edge 58 in the illustrated embodiment. In the illustrated embodiment, the proximal portion of needle hub 32 sits flush with the proximal portion of false wall 60. In some embodiments, this configuration helps to minimize the dead volume within syringe assembly 20; however, other configurations could be used (e.g. the proximal end of needle hub 32 could project slightly in the proximal direction from false wall 60, or could be slightly recessed within a recess 73 of false wall 60, so long as plunger locking tip 31 can readily engage with needle hub 32).

In the illustrated embodiment, false wall 60 is symmetrical about a central radial axis. Thus, false wall 60 is provided with two recesses 73, even though only one of these recesses receives the locking element of needle hub 32. In some embodiments, providing a false wall 60 that is symmetrical about a central radial axis avoids a need to ensure that false wall 60 is inserted with a particular orientation during manufacture of syringe assembly 20.

The central opening 62 of false wall 60 also includes a central receptacle 61 that sealingly engages with the engagement features of needle hub 32, i.e. O-ring 69 and tapered seals 70 in the illustrated embodiment. As a result of the presence of central receptacle 61, which results in the formation of a radial channel on the inside surface of false wall 60, needle hub 32 is restrained from movement in the axial direction by a pair of radially inwardly extending projections 67 on the inside surface of false wall 60. The tapered seals 53 of false wall 60 are provided on the surfaces of projections 67 that contact the correspondingly tapered seals 70 of needle hub 32.

The engagement of needle hub 32 in false wall 60 is sufficiently strong that needle hub 32 is prevented from movement during the application of an injection force or a loading force by a user, but weak enough that movement of false wall 60 produced by the application of a post-injection force via plunger 28 forces false wall 60 to slide distally past needle hub 32, thereby releasing needle hub 32 (and thereby needle 22) for retraction.

Any suitable material can be used for the construction of false wall 60 that allows it to initially retain needle hub 32 and then release needle hub 32 upon application of a post-injection force. In some embodiments, false wall 60 is made from an elastomer having a suitable durometer to release needle hub 32 when a post-injection force is applied.

In the illustrated embodiment, the central opening 62 of false wall 60 is provided with surface features that prevent formation of an airtight seal between false wall 60 and needle hub 32 after needle hub 32 has been displaced from its initial position by the release of propellant from propellant release cell 34. This ensures that a passageway is available for the flow of propellant from propellant release cell 34 (after it has been punctured) to the needle retraction assembly 108 described below. In the illustrated embodiment, the surface features that prevent formation of an airtight seal are channels 71. Channels 71 extend axially along projections 67 of false wall 60 to provide a passageway for the flow of propellant between needle hub 32 and false wall 60 after needle hub 32 has been initially dislodged from false wall 60 (and the seals provided by O-ring seal 69 and tapered seals 70 have thereby been removed) by the application of a post-injection force, to ensure propellant can flow and apply an upstream biasing pressure to needle retraction assembly 108.

With reference to FIGS. 10 and 11A-11C, the locking tip 31 is described in more detail. In the illustrated embodiment, for manufacturing convenience and cost reduction, the locking tip 31 is made as a single part with two components as an overmold: a rigid component 90 for engaging with locking edge 58 of needle hub 32 in a snap-fit engagement and for engaging with capture projections 97 of plunger 28 (as described below), and a more flexible overmolded component 91 that sealingly engages with the interior surface of retraction lumen 29, to prevent medicament from flowing past locking tip 31 and to ensure a good seal so that pressure can be applied by released propellant to move retraction assembly 108 in the proximal direction. Typically, rigid component 90 would be made of a rigid material such as a rigid plastic like polycarbonate or Styrolux™, polypropylene or the like. More flexible component 91 would typically be made of a relatively more flexible material, for example, silicone, thermoplastic elastomer or other similar polymer, or the like.

Rigid component 90 of locking tip 31 has a generally cylindrical shape so that it can fit within plunger lumen 29, and includes at least one locking aperture 92 formed along at least one side thereof. Locking aperture 92 includes a locking edge 85 on a distal edge thereof, for engaging in snap-fit engagement with locking edge 58. Locking aperture 92 engages (via locking edge 85) in a snap-fit with locking edge 58 of needle hub 32 when a user applies a post-injection force, so that locking tip 31, needle hub 32 and needle 22 are joined together to provide an assembly 108 for retraction (referred to herein as a retraction assembly). While in the illustrated embodiment, locking aperture 92 is shown as extending through a portion of rigid component 90, any suitable configuration that allows for snap-fit engagement with locking edge 58 of needle hub 32 could be used. For example, two, three, or more locking apertures could be provided for engagement with locking edge 58. Additionally, while locking channel 92 has been shown as being formed as a slot or aperture through rigid component 90, locking channel 92 could alternatively be formed as a channel on the inside surface of rigid component 90, without extending fully therethrough.

Figure 11C:
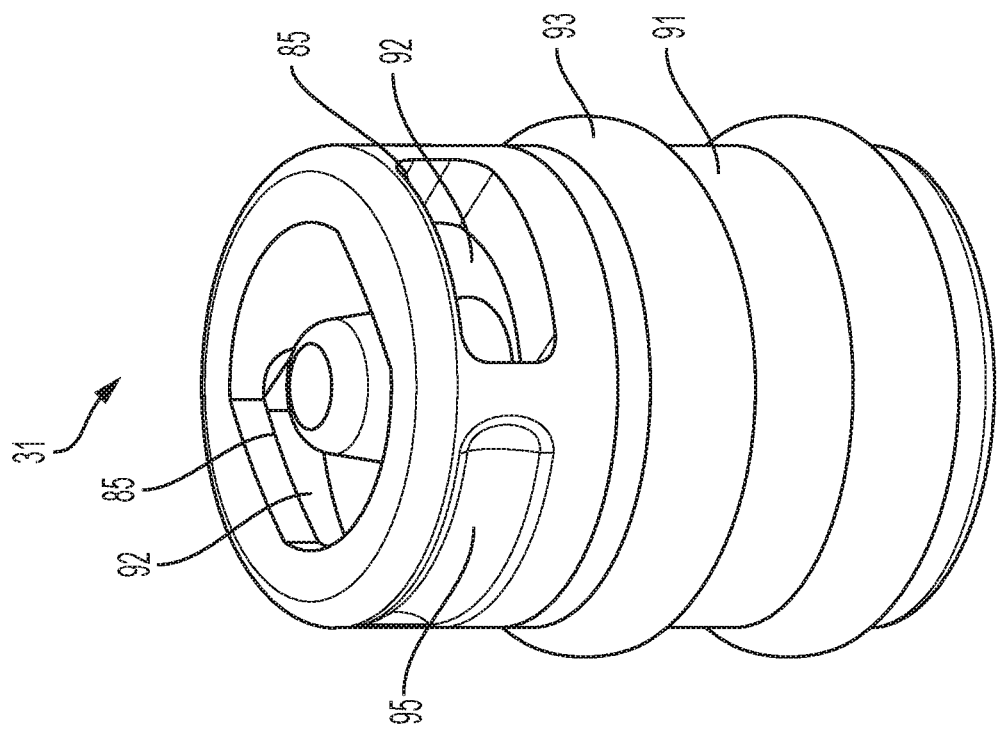
FIG. 11C is a perspective view of the example embodiment of a locking tip shown in FIG. 11A.
Figure 11B:
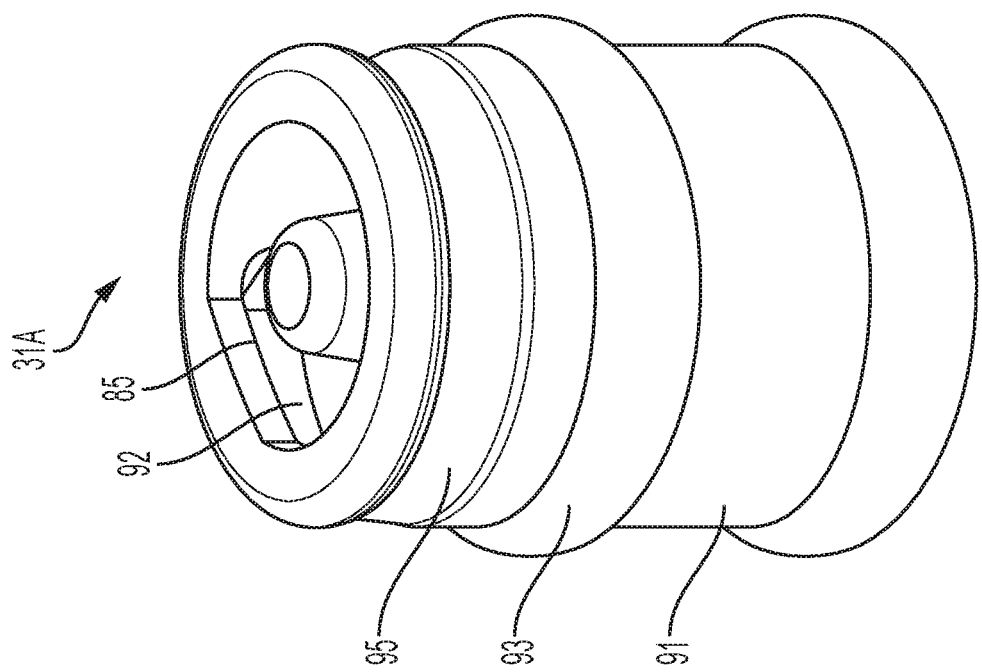
FIG. 11B is a perspective view of a second example embodiment of a locking tip.

In one example embodiment, a single locking aperture 92 is provided on locking tip 31, to minimize the amount of force required to sealingly engage locking tip 31 with needle hub 32. The presence of additional locking apertures 92 may increase the amount of force required to snap locking edge 58 and locking apertures 92 together to sealingly engage locking tip 31 with needle hub 32, and this increased force must be balanced against the other forces required to release needle hub 32 and locking tip 31 for retraction upon application of a post-injection force by a user, as outlined in greater detail below. FIG. 11B shows an example embodiment of a locking tip 31A having only one locking aperture 92, and more clearly shows the distal groove 95 that engages with capture projections 97 on the tip of plunger 28. FIG. 11C shows an example embodiment of a locking tip 31 such as that shown in FIG. 11A, having two locking apertures 92.

Flexible component 91 of locking tip 31 has a pair of sealing rings 93 that are provided by radially outwardly extending protrusions on the outside circumference of generally cylindrical flexible component 91. Different numbers of sealing rings could be used. In some embodiments, the use of two sealing rings rather than just one sealing ring can help to ensure the linear travel of needle assembly 108 during retraction. Sealing rings 93 are sealingly engaged with the inside surface of retraction lumen 29. The sealing engagement between sealing rings 93 and retraction lumen 29 is sufficiently firm, together with the engagement of capture projections 97 with distal groove 95, so that locking tip 31 does not move in response to the application of a loading force or the injection force, but also such that sealing rings 93 permit locking tip 31 (and hence retraction assembly 108) to slideably move within retraction lumen 29 in response to pressure applied by released propellant after the rupture of propellant release cell 34, when capture projections 97 have been disengaged from distal groove 95.

Flexible component 91 of locking tip 31 also includes a central cylindrical projection 89 with a tapered surface 94 that is complementary to tapered surface 57 of needle hub 32 (i.e. tapered surface 94 is tapered inwardly from its proximal end to its distal end), so that engagement of tapered surfaces 94 and 57 when a user applies a post-injection force provides a seal to prevent any further fluid flow through needle 22. Central cylindrical projection 89 is positioned at the distal portion of flexible component 91, and sits within and is axially aligned with rigid component 90 of locking tip 31 so that it can engage with needle hub 32.

Figure 12:
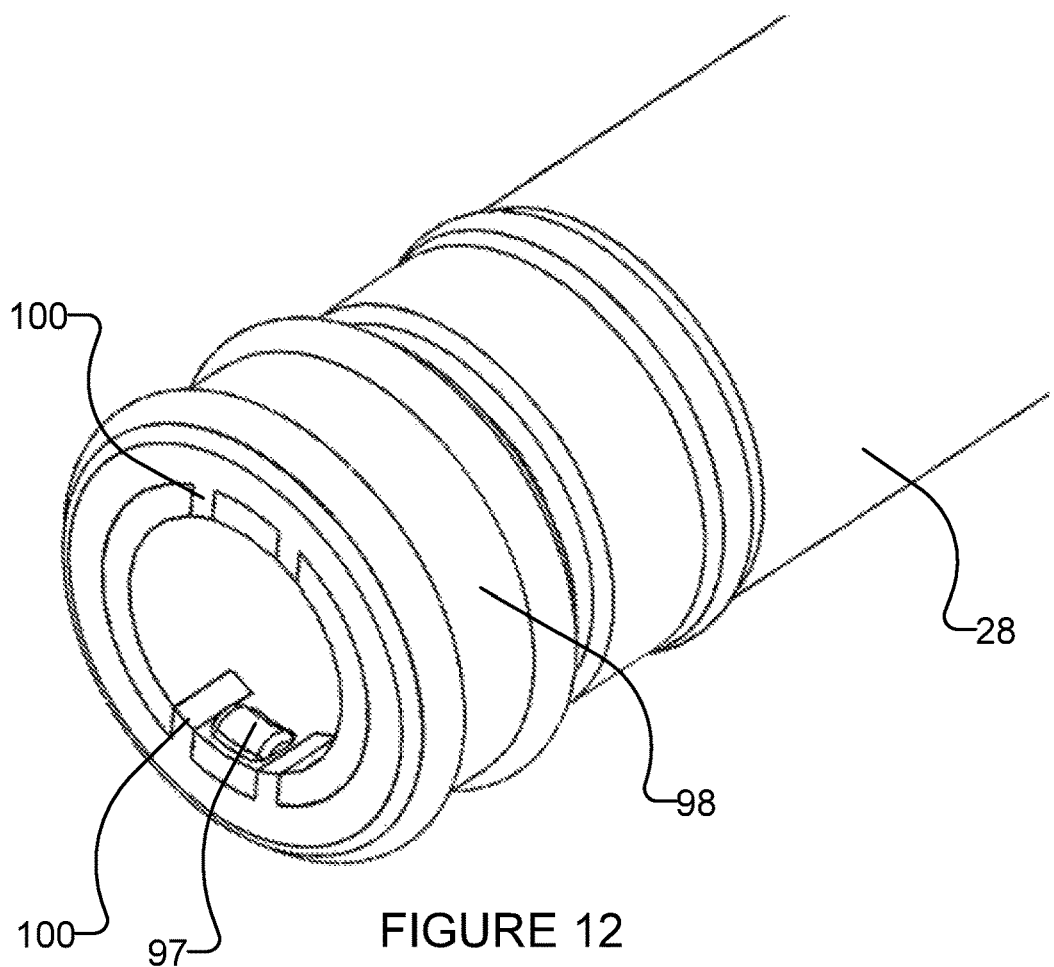
FIG. 12 shows a partial perspective view of a plunger according to one example embodiment.

In some embodiments, including the illustrated embodiment, to facilitate retention of locking tip 31 at the distal end of plunger 28 during the application of a loading force and/or an injection force, locking tip 31 includes one or more distal grooves 95 formed in rigid component 90. Distal groove 95 extends radially inwardly around a distal portion of the outside surface of locking tip 31, and is engageable with one or more radially inwardly extending capture projections 97 formed on the inside surface of the distal end of plunger 28 (FIG. 12). In the illustrated embodiment, two capture projections 97, spaced apart by 180°, are provided. However, other numbers of projections 97 and other configurations could be used (e.g. four capture projections 97, spaced apart by 90°, three capture projections 97 spaced apart by 120°, or even capture projections 97 spaced asymmetrically, although more even retraction of needle assembly 108 is likely to be achieved by keeping capture projections 97 symmetrically spaced).

In alternative embodiments, capture projections 97 and/or distal groove 95 could be omitted, and a different engagement between plunger tip 31 and the distal end of plunger 28 could be used, for example, a sufficiently tight but releasable press or friction fit, connection by easily frangible connectors or a breakable piece of material that prevents plunger tip 31 from releasing during the application of a loading or injection force but allows release of plunger tip 31 in response to a post-injection force, or the like.

The engagement of distal groove 95 and capture projections 97 is broken by the application of a post-injection force by a user. The force required to disengage distal groove 95 from capture projection 97 should be greater than the force required to sealingly engage locking tip 31 with needle hub 32. If the force required to disengage distal groove 95 from capture projection 97 is similar to or less than the force required to sealingly engage locking tip 31 with needle hub 32, then there is a risk that locking tip 31 will disengage from distal groove 95 and be shifted proximally within retraction lumen 29 on the application of a post-injection force by a user, without engaging with needle hub 32. This would result in no retraction of needle 22. In one example embodiment of a syringe having a volume of 3 mL and an overall actuation force (i.e. the minimum post-injection force that has to be applied by a user to cause retraction of needle 22) of approximately 7 lbs for retracting needle 22, the force required to sealingly engage locking tip 31 with needle hub 32 is less than 1 lb, and in some embodiments is in the range of about 0.7 lbs, while the force required to disengage distal groove 95 from capture projections 97 is greater than 2 lbs, and in some embodiments is in the range of 2.5 lbs.

In the illustrated embodiment, capture projections 97 are formed on a region of plunger 28 located between two axially extending channels 100 in the distal end of plunger 28. In some embodiments, positioning of capture projections 97 between channels 100 provides a degree of flexibility to the region of plunger 28 bearing projections 97, which may facilitate molding of projections 97 in the manufacture of plunger 28. In some embodiments, channels 100 are omitted.

In the illustrated embodiment, plunger seal 98 is manufactured as an overmold to plunger 28. In such embodiments, plunger seal 98 is an elastomeric overmold, and channels 100 are filled with the elastomer overmold. In other embodiments, plunger seal 98 is manufactured as a separate part from plunger 28 and the two elements are joined together in any suitable manner, for example by a sufficiently tight friction fit, use of suitable adhesives, or the like. Plunger seal 98 sealingly but slidingly engages the interior surface 44 of syringe 24 to facilitate injection of medicament in a similar manner to conventional syringes.

Needle 22 is hollow and has a downstream tip 52 (FIGS. 1 and 2) for injection of medicament into a subject and an upstream intake opening 54 (FIG. 8) for receiving medicament from medicament chamber 30. In some embodiments, a needle seal 56 (FIG. 2) is provided to seal the distal end of syringe 24. In some embodiments, needle seal 56 more tightly seals propellant release chamber 36 by sealingly engaging against needle 22, to enhance the seal between the outer diameter of needle 22 and needle guide 80 and prevent the escape of released propellant along the outer diameter of needle 22 when the propellant is released in propellant release chamber 36. In some embodiments, needle seal 56 is secured to the needle guide 80 in any suitable manner, for example by suitable adhesives, by compression fit between needle guide 80 and syringe barrel 26 or between portions of needle guide 80, overmolding, or the like. In some embodiments, needle seal 56 could be integrated with an overmold of needle guide 80. In some embodiments, needle seal 56 may assist in retaining needle 22 within syringe 24 once needle 22 has been retracted by providing a barrier to needle re-emergence. In some embodiments, needle seal 56 may help to prevent any medicament from dripping off the end of needle 22 and into the surrounding environment after use.

Needle seal 56 may be made of a soft, flexible material, for example, polyisoprene. In some embodiments, needle seal 56 is made from silicon or rubber. In some embodiments, needle seal 56 is made from a soft surgical-grade rubber or silicon such that, when needle 22 is retracted, needle seal 56 closes and self-seals the hole left by needle 22. In embodiments in which needle seal 56 is made from polyisoprene, it is possible to puncture needle seal 56 using needle 22 during assembly of syringe assembly 20, which may avoid a need to slit needle seal 56 with a blade prior to assembly.

A propellant release cell 34 is contained within syringe barrel 26 distally of needle hub 32, within propellant release chamber 36. In the illustrated embodiment, propellant release chamber 36 is defined between the distal tip of syringe barrel 26, needle guide 80, and needle hub 32. Depending on the configuration of the components of syringe assembly 20, the propellant release chamber 36 could be defined between other components of the assembly, depending on the specific configuration of components used. The propellant release chamber 36 confines propellant released by propellant release cell 34 so that the propellant exerts a force on the locking tip 31 and needle hub 32 to retract needle 22 in the proximal direction. Propellant release cell 34 is oriented within propellant release chamber 36 so that sealing membrane 48 faces towards puncture lances 38. In the illustrated embodiment, the elongate central neck 84 of needle guide 80 (described below) has a generally cylindrical shape, and is received within central aperture 49 of propellant release cell 34.

In some embodiments, plunger 28 and syringe barrel 26 include a plunger locking feature to retain plunger 28 in a position at or near the distal limit of travel of plunger 28. In some embodiments, the locking feature secures plunger 28 in place within syringe barrel 26 during needle retraction. In some embodiments, the locking feature prevents tampering with or re-use of syringe assembly 20 after it has been used and needle 22 has been retracted.

Figure 13:
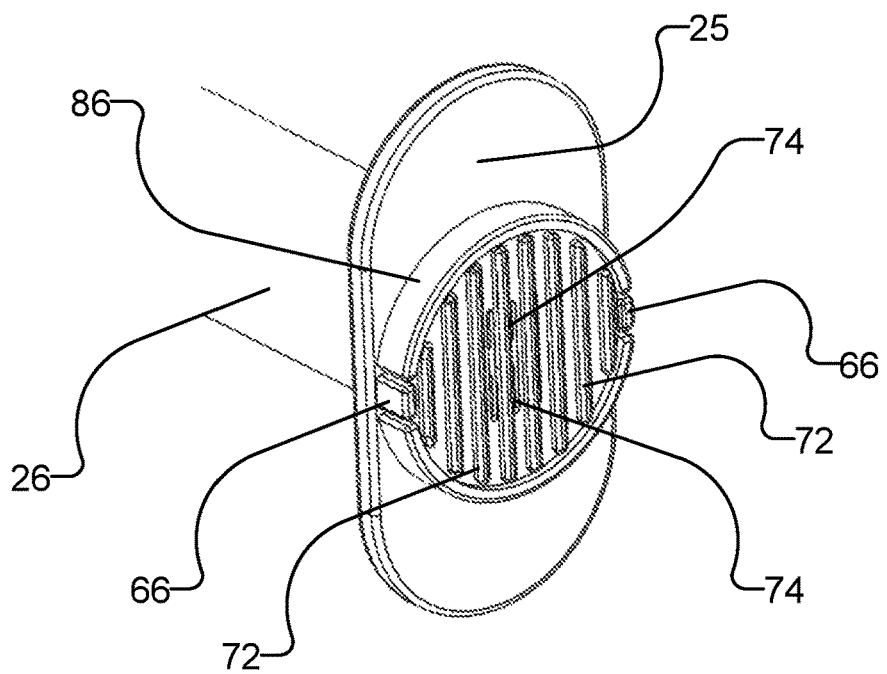
FIG. 13 is a perspective view showing the engagement of a plunger locking feature to lock the plunger at or near its downstream (i.e. distal) limit of travel according to one example embodiment.
Figure 14:
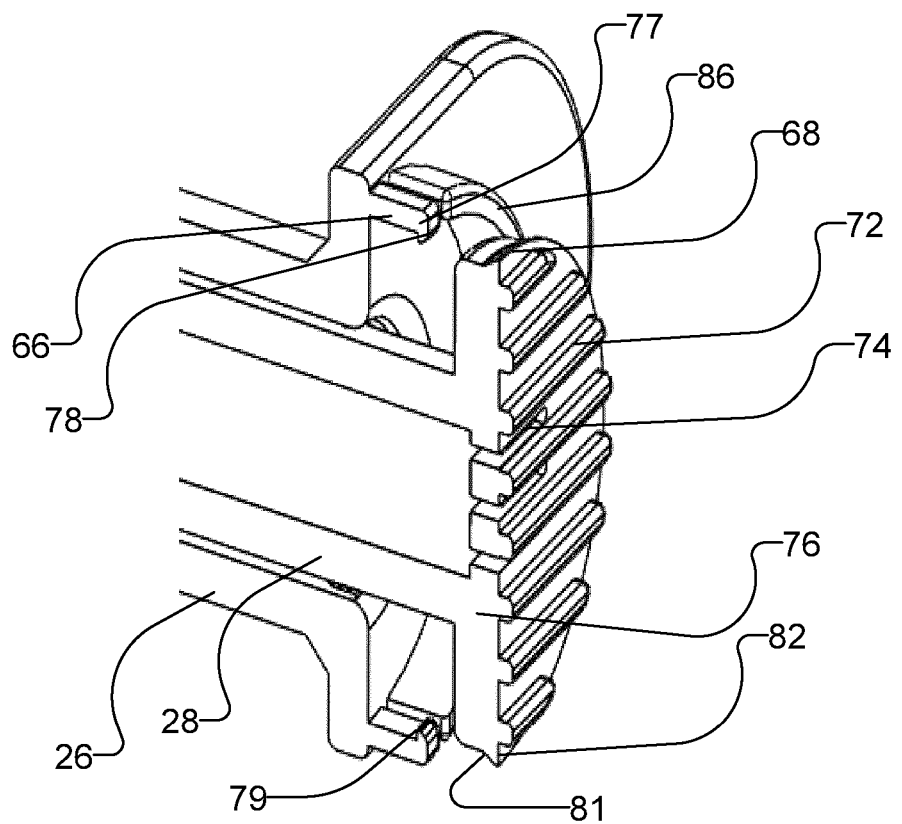
FIG. 14 is a cross-sectional view showing the example plunger locking feature of FIG. 13 in more detail, with the plunger slightly withdrawn from the syringe barrel.

In the illustrated embodiment with reference to FIGS. 13 and 14, the plunger locking feature is provided by snap-fit engagement members 66, 68 positioned at the proximal end of each of syringe barrel 26 and plunger 28. In the illustrated embodiment, a syringe snap-fit engagement member 66 provided at the proximal end of syringe barrel 26 projects in the proximal direction from the proximal end of syringe barrel 26, and has a radially inwardly extending locking projection 77 at its proximal end. Locking projection 77 has an inwardly angled sliding surface 78 past which a corresponding angled sliding surface 81 of plunger 28 can slide (inwardly angled sliding surface 78 is angled inwardly and distally relative to the outside edge of locking projection 77), and a radially extending locking surface 79 located distally of sliding surface 78. Locking surface 79 is configured to lock with corresponding locking surface 82 of plunger 28. In the illustrated embodiment, locking surface 79 extends generally straight in the radial direction and locking surface 82 likewise extends generally straight in the radial direction, so that once locking surface 82 slides past angled sliding surface 78 and engages with locking surface 79, plunger 28 cannot thereafter be withdrawn from syringe barrel 26. In alternative embodiments, other configurations that prevent plunger 28 from being slid out of syringe barrel 26 after the plunger locking feature has been engaged can be used.

Plunger snap-fit engagement member 68 has an outwardly angled sliding surface 81 that can slide past inwardly angled sliding surface 78, and a generally radially extending locking surface 82 that can slide past and engage with locking surface 79. Angled sliding surface 81 has a shape that is complementary to angled sliding surface 78 (angled outwardly and in the proximal direction relative to the proximal end of plunger 28 in the illustrated embodiment), and alternative complementary shapes that can slide past one another, e.g. slightly curved surfaces, could be used for surfaces 78, 81 in alternative embodiments. In use, at or just before the end of the application of a post-injection force, a user will cause angled sliding surfaces 78, 81 to move past one another, allowing locking surfaces 79, 82 to come into contact in a snap-fit engagement, thereby locking plunger 28 within syringe 24.

In the illustrated embodiment, two pairs of snap-fit engagement members 66, 68 are provided, one on each opposing side of syringe assembly 20. Any desired number and location of snap-fit engagement members 66, 68 could be used (e.g. three, four or more pairs of snap-fit engagement members 66, 68), so long as these can be used to lock plunger 28 within syringe 24.

In the illustrated embodiment, a further mechanism is provided for preventing tampering or re-use of syringe assembly 20 after use. A generally circular anti-tamper ring 86 is provided that is shaped and positioned to receive therein the correspondingly shaped generally circular proximal end of plunger 28. Anti-tamper ring projects axially in the proximal direction from the proximal end of syringe 24, to generally surround the end of plunger 28. Thus, when snap-fit engagement members 66, 68 are engaged in a snap-lock fit, generally circular ring 86 encircles the proximal end of plunger 28. Thus, if a user wished to try to pry apart or tamper with plunger 28 and syringe 24 (for example, in an effort to re-create and re-use syringe assembly 20), generally circular ring 86 would provide a barrier to help prevent the user from forcing a tool underneath the distal end of plunger 28 in an effort to pry apart plunger 28 and syringe 24. While a generally circular shape is described and illustrated, other corresponding shapes could be used for the distal end of plunger 28 and generally circular ring 86 (e.g. oval or other desired shape), so long as generally circular ring 86 is able to surround the distal end of plunger 28 and prevent a user from inserting tools to pull plunger 28 apart from syringe 24. In some embodiments, generally circular ring 86 is omitted.

In some embodiments, plunger 28 includes one or more passageways, such as vent holes 74, formed therethrough. In some embodiments, vent holes 74 allow release of air from retraction lumen 29 upstream of needle hub 32 and locking tip 31 when needle 22 is retracted. In some embodiments, vent holes 74 are positioned proximally at or close to the upstream limit of travel of retraction assembly 108 when fully retracted, to avoid a loss of propellant pressure (and resultant upstream biasing force) that could stop the upstream travel of needle 22 before it has been fully retracted as could occur if, for example, vent holes 74 are positioned too far distally of the upstream limit of travel of needle assembly 108. In the illustrated embodiment, vent holes 74 are provided through the distal end of plunger 28, so that the region of retraction lumen 29 upstream of locking tip 31 is placed in fluid communication with the outside atmosphere. In some embodiments in which an excess propellant venting mechanism such as vent 110 (described below) is provided, vent holes 74 are omitted and all venting is done through vent 110.

In some embodiments, plunger 28 includes a plunger end flange 76 to provide a bearing surface for the fingers of a user, e.g. to facilitate pulling plunger 28 in the proximal direction within syringe barrel 26 to draw liquid into medicament chamber 30 and/or administration of medicament using syringe assembly 20.

In some embodiments, plunger 28 includes a plurality of thumb ridges 72 on the distal portion of plunger 28 and/or on plunger end flange 76. In some embodiments, thumb ridges 72 prevent a user's fingers from occluding vents 74.

Figure 15:
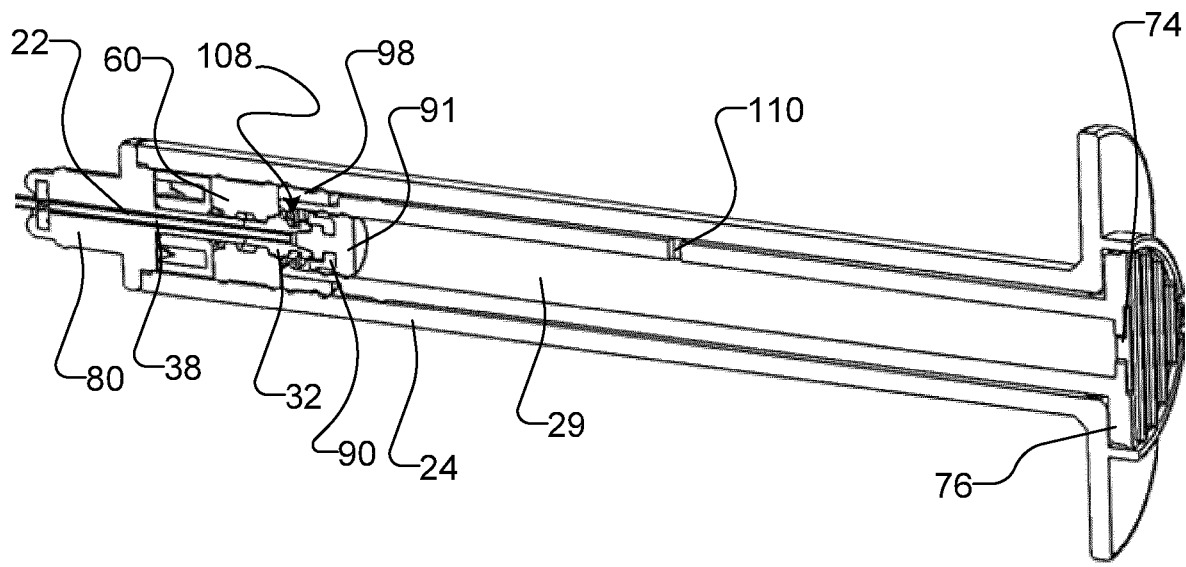
FIG. 15 is a cross-sectional view showing an excess propellant venting mechanism according to an example embodiment.

In some embodiments, plunger 28 includes an excess propellant venting mechanism for venting any residual propellant remaining after retraction of needle 22 has been fully completed. With reference to FIG. 15, in some embodiments, a propellant vent 110 is provided through plunger 28. Propellant vent 110 is provided a sufficient distance proximally of locking tip 31 so that the total combined length of retraction assembly 108 can be received within syringe barrel 26 distally of propellant vent 110, so that no part of needle 22 projects outside of syringe 26 after retraction. In use, retraction assembly 108 moves proximally within retraction lumen 29 in response to the force applied by released propellant. Air that is located upstream of locking tip 31 is forced out vent holes 74 and/or 110. After needle 22 has been fully retracted, locking tip 31 can continue moving proximally past propellant vent 110. Once locking tip 31 moves proximally past propellant vent 110, a passageway is opened in the gap between plunger 28 and syringe 24 so that any excess propellant can escape syringe assembly 20. That is, once locking tip 31 moves proximally past propellant vent 110, propellant release chamber 36 is in fluid communication with the outside atmosphere. In some embodiments, the provision of propellant vent 110 as aforesaid avoids holding any excess pressure released from propellant release cell 34 within syringe assembly 20 after needle 22 has been retracted. In some embodiments, two, three, four or more propellant vents 110 could be provided and spaced apart about the circumference of plunger 28, but should be positioned axially at a similar distance proximally of locking tip 31, so that the retraction assembly 108 will be retracted to the desired location within retraction lumen 29.

Figure 21:
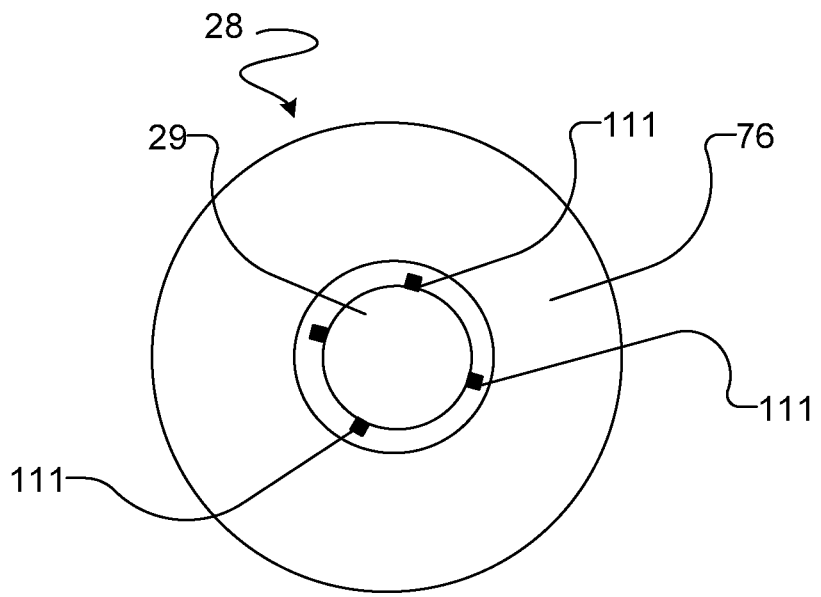
FIG. 21 is a top view showing an example embodiment of a plunger having grooves or keyways in an interior surface of the plunger for venting excess propellant after needle retraction.
Figure 22:
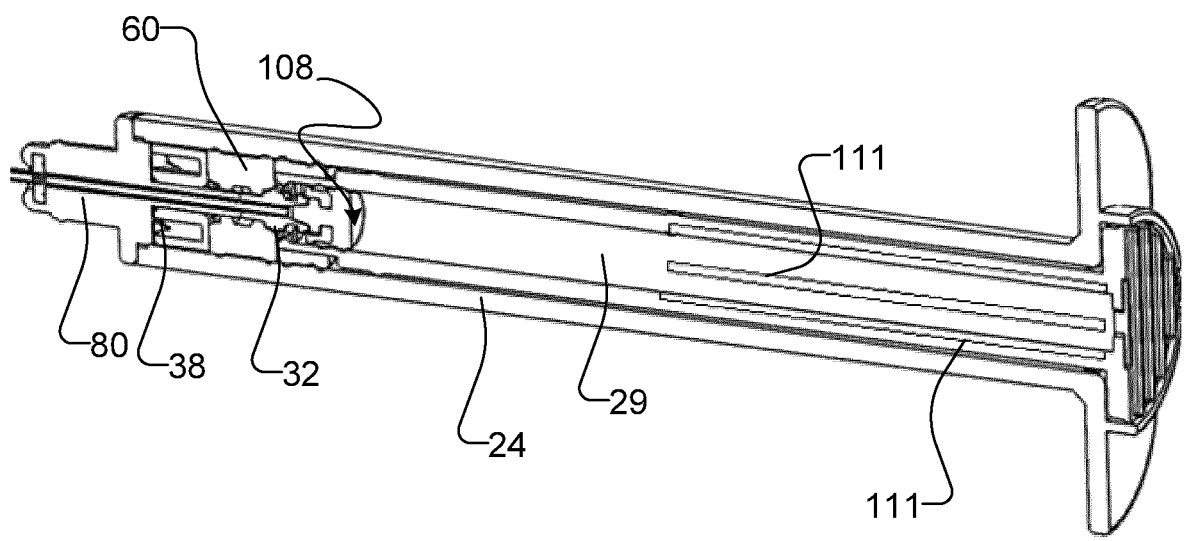
FIG. 22 is a cross-sectional view of an example embodiment of a plunger having grooves or keyways in an interior surface of the plunger for venting excess propellant after needle retraction.

In alternative embodiments, as illustrated in FIGS. 21 and 22, propellant vent apertures 110 could be removed, and venting of any residual propellant can be achieved by providing a series of grooves or keyways 111 on the inside surface of retraction lumen 29. Grooves or keyways 111 are positioned axially within retraction lumen 29 so that they start distally at approximately the location where propellant vent aperture 110 would be positioned (i.e. a sufficient distance proximally of locking tip 31 so that the retraction assembly 108 will be retracted to the desired location within retraction lumen 29). Grooves or keyways 111 extend proximally along the interior surface of retraction lumen 29 to the very proximal portion of retraction lumen 29, so that propellant can travel out of retraction lumen 29. In some such embodiments, suitably positioned vent holes 74 or other suitable venting mechanism are provided on plunger end flange 76, so that propellant can escape from the proximal end of retraction lumen 29 even when plunger 28 has reached the farthest distal limit of its travel within syringe 24. In some embodiments, propellant vent aperture 110 and grooves or keyways 111 could both be present, so long as a path of fluid communication for propellant flow is provided between an appropriate axial location within retraction lumen 29 (i.e. just distal of the upstream limit of retraction of locking tip 31 when needle 22 is retracted) and the external atmosphere.

In some embodiments, propellant release cell 34 is initially secured within propellant release chamber 36 in any suitable manner to minimize the risk that sealing membrane 48 may be prematurely punctured by puncture lances 38. For example, the outer surface of shell 46 of propellant release cell 34 may be frictionally engaged with the inner surface 44 of syringe barrel 26, or with elongate central neck 84 of needle guide 80 (described below), or propellant release cell 34 may be initially affixed to engagement ring 60, or central neck 84 in any suitable manner, such as by adhesives or the like. In embodiments including the illustrated embodiment in which movement of propellant release cell 34 is required to puncture propellant release cell 34 upon application of a post-injection force, the adhesives used should be sufficiently weak to allow propellant release cell 34 to move upon application of a post-injection force, but sufficiently strong to retain propellant release cell 34 in position during application of a loading force or an injection force.

In some embodiments, propellant release cell 34 is not specifically secured within propellant release chamber 36 in any manner (i.e. propellant release cell 34 is free floating), and the material that sealing membrane 48 is made from is sufficiently strong that mere contact with puncture lances 38 (e.g. as might occur during shipping or loading of syringe assembly 20) in the absence of force applied by a user as a post-injection force is not sufficient to rupture propellant release cell 34.

The pressure and volume of propellant in propellant release cell 34 should be sufficient to ensure that needle 22 is fully retracted within retraction lumen 29 when propellant release cell 34 is punctured. Propellant release cells intended for use with a larger volume of syringe may have a larger volume (and thus contain more propellant) than propellant release cells intended for use with a smaller volume of syringe. The appropriate pressure and volume of propellant to be included in propellant release cell 34 can be determined by one skilled in the art based on the propellant to be used and the anticipated range of temperatures at which syringe assembly 20 will be used.

A mechanism for puncturing sealing membrane 48 of propellant release cell 34 in response to a post-injection force is provided within propellant release chamber 36. In the illustrated embodiment, a propellant release trigger in the form of one or more puncture lances 38 is provided. Puncture lances 38 are secured within syringe barrel 26 in any suitable manner. In the illustrated embodiment, puncture lances 38 are formed as part of needle guide 80 secured at a distal portion of syringe barrel 26. In alternative embodiments, puncture lances 38 are secured directly to the distal end of syringe barrel 26.

Puncture lances 38 could alternatively be mounted to appropriate portions of false wall 60, or to the distal end of plunger 28 (with corresponding holes provided through false wall 60 to allow the puncture lances to pass therethrough), or integrally formed with such components, such that puncture lances 38 are positioned and disposed to be operable to puncture propellant release cell 34 in response to application of a post-injection force. In such embodiments, the orientation of propellant release cell 34 would be reversed by 180°, so that sealing membrane 48 is oriented towards puncture lances 38 to facilitate rupture upon application of a post-injection force. In alternative embodiments, propellant release cell 34 is made entirely from a rupturable material (i.e. does not include any rigid walls such as shell 46), and therefore so long as the propellant release cell is positioned so that it will be contacted by the rupture mechanism upon the application of a post-injection force, the orientation of propellant release cell 34 would not matter.

Figure 16:
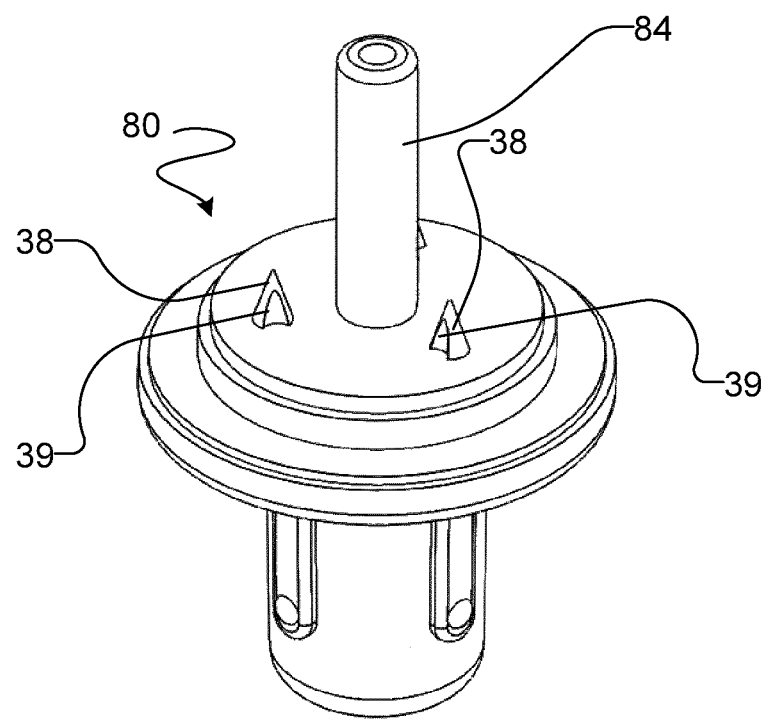
FIG. 16 shows exemplary puncture lances on an example embodiment of a needle guide.

In the illustrated embodiment, with reference to FIG. 16, three puncture lances 38 are provided for puncturing propellant release cell 34 in response to the application of a post-injection force by a user. Any desired number of puncture lances could be used, for example two, four, five, six or more. Puncture lances 38 need not be symmetrically disposed, but providing puncture lances 38 in a symmetrical orientation may assist in ensuring reliable rupture of propellant release cell 34.

Each puncture lance 38 has a generally conical shape, and is oriented so that its sharp end projects towards propellant release cell 34 (i.e. proximally in the illustrated embodiment). In the illustrated embodiment, each puncture lance 38 is provided with lateral indentations 39. Lateral indentations 39 help to ensure that propellant flow paths created during puncture of propellant release cell 34 do not become occluded by sealing membrane 48 of propellant release cell 34. In some embodiments, lateral indentations 39 are omitted.

In the illustrated embodiment, puncture lances 38 are manufactured as part of needle guide 80. Puncture lances 38 project towards propellant release cell 34, i.e. project proximally in the same direction as elongate central neck 84 of needle guide 80 in the illustrated embodiment. Needle guide 80 is secured at the distal end of syringe 24 in any suitable manner, for example by friction fit, suitable adhesives, bonding, spin welding, or the like. In one example embodiment, needle guide 80 is ultrasonically welded to syringe body 26 at its distal end.

Figure 17:
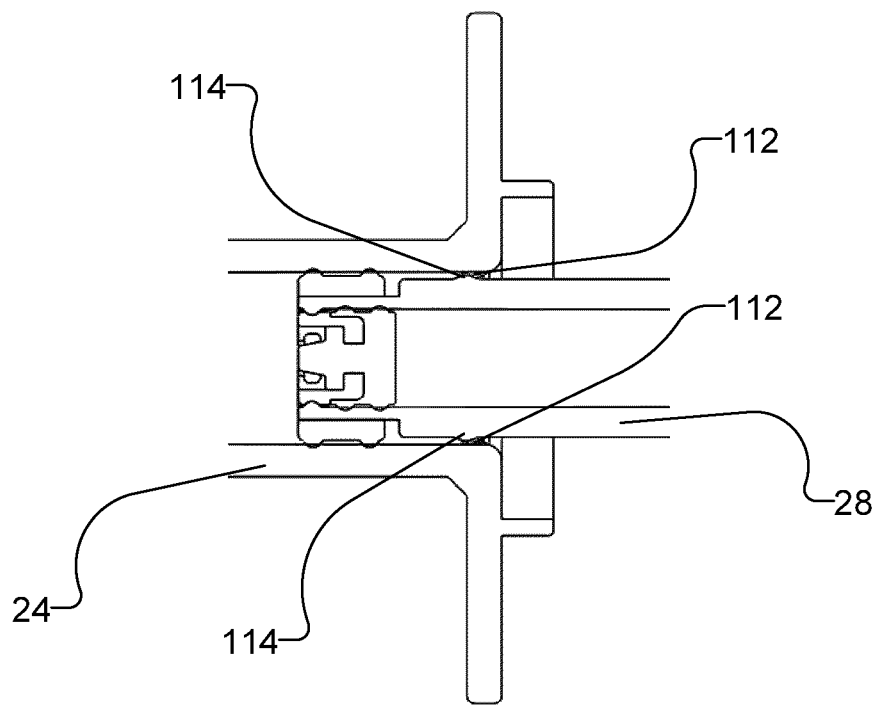
FIG. 17 shows the plunger retention features on an example embodiment.

In some embodiments, to prevent plunger 28 from being fully withdrawn from syringe 24 by a user, plunger retention features are provided. In the illustrated embodiment, with reference to FIG. 17, in some embodiments an interior projection 112 is provided at the proximal end of syringe 24 and a corresponding exterior projection 114 is provided at a distal portion of plunger 28. Projections 112, 114 are shaped and positioned so that plunger 28 can be inserted into syringe 24, but cannot thereafter be removed from syringe 24, or at least cannot be removed without considerable difficulty. In other words, projections 112 and 114 allow for one-way movement of plunger 28 into but not out of syringe 24.

In use, needle cap 50 may be removed in any suitable manner to expose needle 22. Downstream force is applied by a user to the upstream plunger end flange 76 to eject air out of medicament chamber 30, if necessary. When nearly all of the air has been forced out of medicament chamber 30, but before snap-fit engagement members 66, 68 engage, the tip 52 of needle 22 can be submerged in liquid medicament contained in a supply vial, which may be of a conventional type.

Medicament or other liquid for injection is drawn into medicament chamber 30 by withdrawing plunger 28 proximally relative to syringe barrel 26 in the same manner as a conventional syringe, applying a loading force. After medicament chamber 30 has been filled with the desired volume of medicament, air may be removed in the conventional manner by inverting syringe assembly 20 so that needle 22 is pointing upwardly, tapping syringe 24 to displace any air therewithin and allowing the air to float above the medicament, and applying a distally-directed force to the plunger 28 so that residual air is forced out through needle 22.

Needle 22 is positioned at an injection site of a subject in the conventional manner. Medicament can be discharged from medicament chamber 30 by applying a distally-directed force (an injection force) on plunger end flange 76 in a conventional manner, thus causing plunger seal 98 to exert a distal biasing pressure on the medicament contained in chamber 30. The distally-directed biasing pressure is sufficient to force medicament through needle 22. However, the pressure is not sufficient to overcome the frictional force securing false wall 60 to the inner surface of syringe barrel 26 or the frictional force securing needle hub 32 in false wall 60, nor is the corresponding upstream pressure on the tip of plunger 28 sufficient to overcome the frictional force between locking tip 31 and plunger 28.

Figure 18:
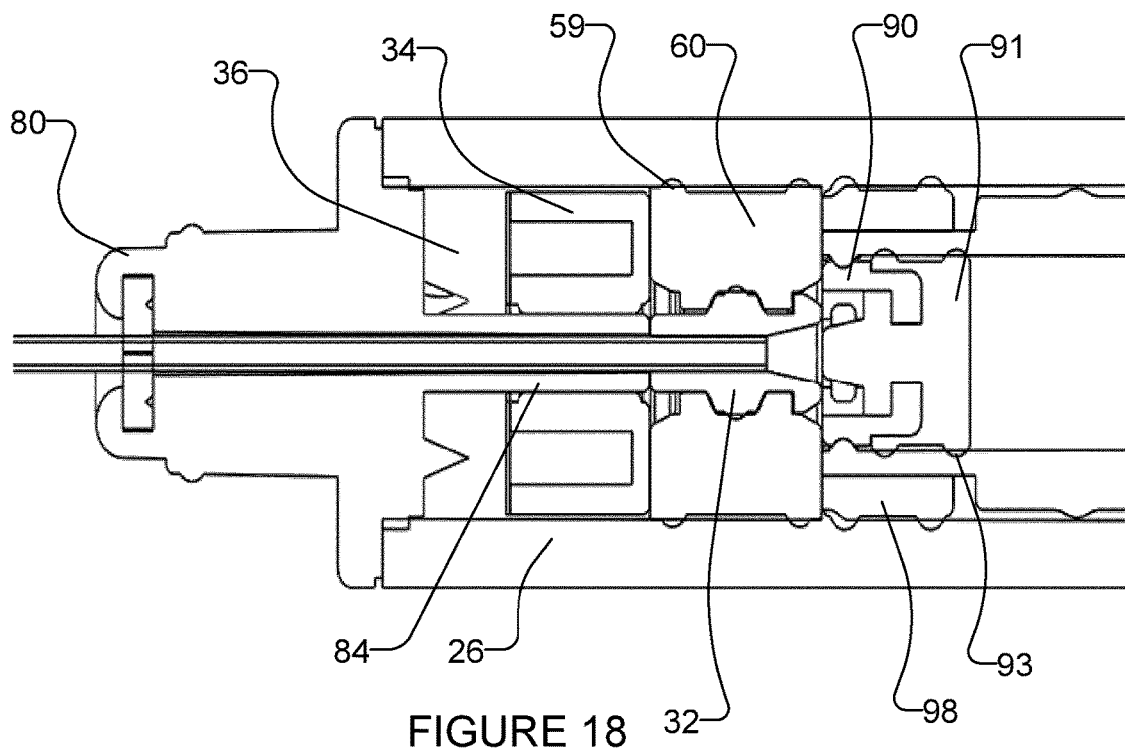
FIG. 18 is a cross-sectional view of a syringe assembly showing an example embodiment of the device after injection of medicament has been completed, just before a user applies a post-injection force.

With reference to FIG. 18, an example embodiment of a syringe assembly 20 is illustrated at the end of the injection stroke, after all or substantially all of the medicament has been injected into a subject. Once the user is ready to actuate the retraction mechanism, a user continues to apply force, now a post-injection force, in the distal direction against plunger 28.

Because application of a post-injection force must cause mechanical movement of components of syringe assembly 20 as described below, the force that must be applied as a post-injection force is greater than the force applied as an injection force. The injection force required to conduct any given injection can vary, for example due to unusually high flow resistance in the tissue of a particular patient. In typical scenarios, it is anticipated that an injection force would be on the order of less than about 1.5 lbs for an exemplary 3 mL syringe, and a post-injection force would be on the order of about 5-7 pounds.

Figure 9D:
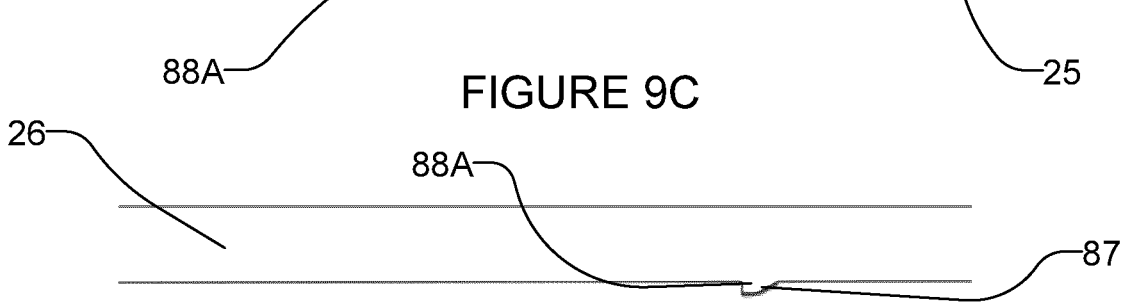
FIG. 9D is a partial cross-sectional view of an example embodiment of a syringe barrel showing the configuration of an example embodiment of a false wall retaining feature.
Figure 9D:
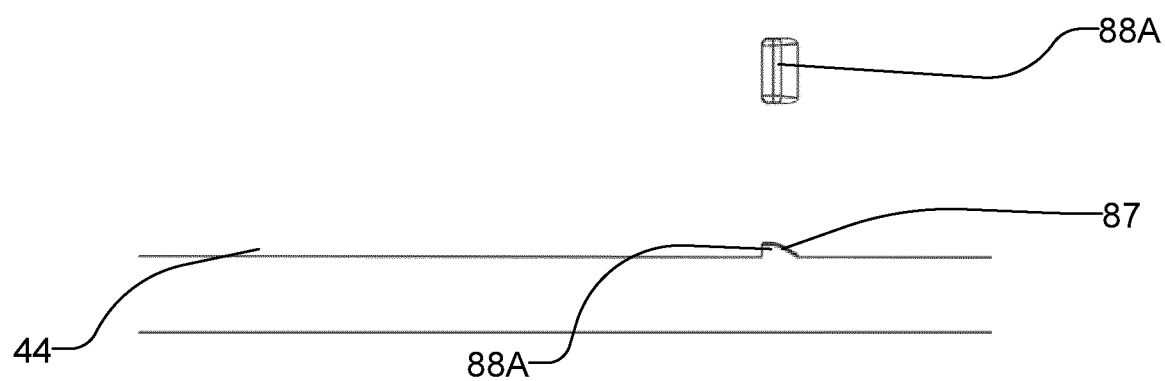
Figure 19:
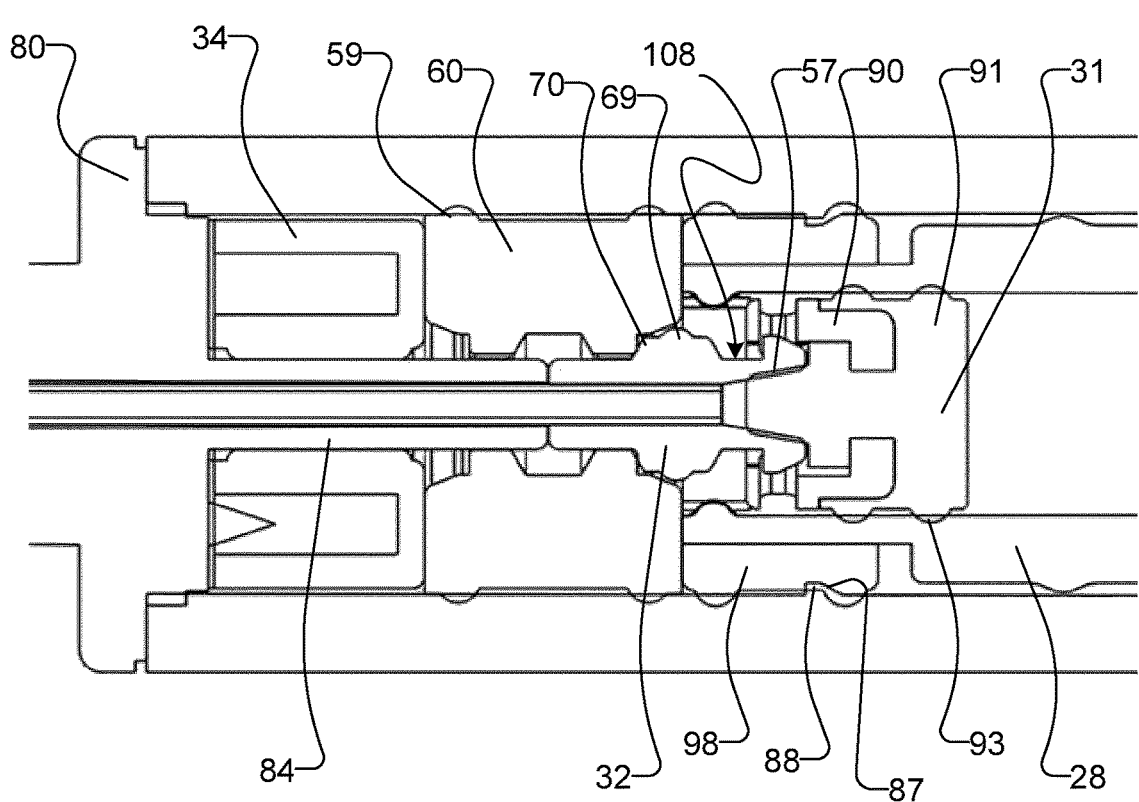
FIG. 19 is a cross-sectional view of a syringe assembly showing an example embodiment of the device after the application of a post-injection force by a user, after a needle retraction assembly has been created and just before the needle retraction assembly is retracted in response to pressure applied by released propellant.

With reference to FIG. 19, continued movement of plunger 28 in response to the application of the post-injection force moves the distal tip of plunger 28 and plunger seal 98 distally over false wall retention feature 88 (or 88A in some embodiments). In the illustrated embodiment, false wall retention feature 88 has a proximal angled portion 87 (FIGS. 2 and 9D). Proximal angled portion 87 slopes radially outwardly in the proximal direction between false wall retention feature 88 and the interior surface 44 of syringe barrel 26. In some embodiments, proximal angled portion 87 facilitates plunger seal 98 sliding over false wall retention feature 88 as a user applies a post-injection force, which may help to reduce the amount of force a user must apply to retract needle 22.

As the distal tip of plunger 28 moves past false wall retention feature 88, plunger 28 applies a distal force against false wall 60, causing false wall 60 to move in the distal direction. As false wall 60 moves in the distal direction, needle hub 32 separates from false wall 60, because needle hub 32 is prevented from moving in the distal direction by elongate central neck 84 of needle guide 80. This causes seals 69 and 70 to release, and false wall 60 is moved distally relative to needle hub 32.

Continued movement of false wall 60 in the distal direction also causes locking tip 31 of plunger 28 to slide over tapered portion 57 of the needle hub 32, so that locking edge 58 of needle hub 32 engages with locking channel 92 of locking tip 31. Needle hub 32 (together with needle 22) thereby becomes engaged with locking tip 31 to provide retraction assembly 108. Also, at the same time, tapered surface 94 of central projection 89 of locking tip 31 is brought into sealing contact with tapered surface 64 of needle hub 32, so that further flow of fluids through needle 22 is prevented. After locking tip 31 becomes engaged with needle hub 32, plunger tip 31 is disengaged from the tip of plunger 28 by the release of capture projections 97 from distal groove 95 by the continued application of a post-injection force, which continues to move the distal end of plunger 28 in the distal direction while central neck 84 of needle guide 80 prevents distal movement of retraction assembly 108, including locking tip 31.

Further movement of false wall 60 in the distal direction causes movement of propellant release cell 34 in the distal direction, causing puncturable membrane 48 of propellant release cell 34 to contact and be punctured by puncture lances 38. This releases propellant from propellant chamber 47 of propellant release cell 34 within propellant release chamber 36.

The released propellant remains under pressure within the confines of the propellant release chamber 36, and therefore a proximal force is applied against needle retraction assembly 108.

With reference to FIG. 18, an example embodiment showing the propellant release chamber 36 in more detail is illustrated. In the illustrated embodiment, propellant release chamber 36 is defined between the distal end of syringe barrel 26, needle guide 80, false wall 60, and needle hub 32. Upon puncture of propellant release cell 34, the propellant contained therein is released within propellant release chamber 36. The released propellant is sealed within propellant release chamber 36 by the engagement of needle guide 80 and needle seal 56 with syringe barrel 26 and needle 22, and by the sealing engagement of o-ring features 59 of false wall 60 with the interior surface 44 of syringe barrel 26. The compressed propellant is thus constrained to move within the barrel of syringe 26 in the proximal direction towards a distal bearing surface 102 (FIG. 20) of retraction assembly 108, which is provided by plunger locking tip 31 in the illustrated embodiment. The compressed propellant is prevented from escaping past retraction assembly 108 by the engagement of sealing rings 93 of locking tip 31 with the interior walls of retraction lumen 29, and by the engagement of tapered surfaces 94, 64 on locking tip 31 and needle hub 32, respectively. The released propellant therefore exerts a force in the proximal direction against distal bearing surface 102, thereby causing retraction assembly 108 to move in the proximal direction.

Figure 20:
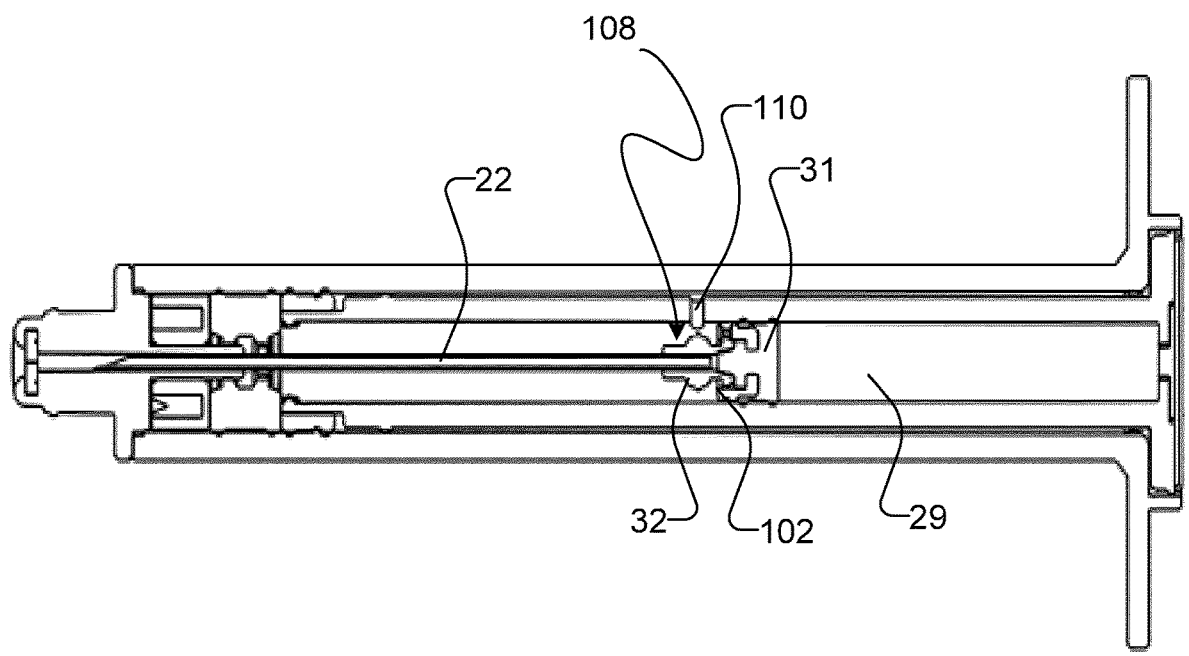
FIG. 20 is a cross-sectional view of an example embodiment of a syringe assembly showing the needle retraction assembly in its fully retracted position.

The proximally-directed biasing pressure causes needle retraction assembly 108 to slide proximally into retraction lumen 29, thus retracting needle 22 within retraction lumen 29 (FIG. 20 versus FIG. 15). The volume and pressure of propellant in propellant release cell 34 should be sufficient to retract the full length of needle 22 inside the syringe barrel 26, so that the downstream tip 52 of needle 22 does not project outside of syringe 24 and thereby pose a biohazard. Any excess propellant pressure is vented after locking tip 31 passes propellant vent 110 along its continued path of travel in the proximal direction. After locking tip 31 passes propellant vent 110, the propellant will no longer exert a distal biasing pressure against retraction assembly 108, and retraction assembly 108 will come to a rest within retraction lumen 29, as illustrated in FIG. 20.

Suitable materials for the manufacture of syringe assembly 20 may be selected by one skilled in the art. For example, syringe barrel 26 and plunger 28 may be made from any suitable plastic or thermoplastic, for example, polycarbonate, acrylic, copolyester, SBC (e.g. Styrolux™), or the like. Plunger seal 98 may be made from any suitable material, for example silicone, thermoplastic elastomers, or the like. In some embodiments, plunger seal 98 may be a self-lubricating seal. In some embodiments, syringe barrel 26 and/or plunger seal 98 may be treated with a medical grade lubricant. Needle 22 may be made of medical grade needle tubing. The compressed propellant used in propellant release cell 34 may be any suitable propellant, for example a pharmaceutical-grade hydrofluorocarbon such as heptafluoropropane, 1,1,1,2-tetrafluoroethane or medical-grade nitrogen. In some embodiments, heptafluoropropane is the propellant, and is selected based on its expansion properties and lack of toxicity. Suitable materials for manufacture of propellant release cell 34 include suitable polymers such as, for example, nylon, polyethylene, polypropylene, polystyrene or the like, or suitable copolymers thereof. Components may be sterilized prior to packaging in any suitable manner, for example with e-beam radiation, γ-radiation, or ethylene oxide (EtO) gas. The materials selected for manufacture of syringe assembly 20 should be compatible with the medicament to be administered to the subject.

In some embodiments, syringe 24 is a prefilled syringe, i.e. syringe 24 has been filled with a predetermined quantity of a specified medicament. In use, prefilled syringe 24 does not need to be loaded with medicament, but can simply be used to inject the medicament already contained therein in a subject in the manner described above, followed by retraction of needle 22.

In some embodiments, the portions of syringe barrel 26 through which components of the retraction mechanism (e.g. false wall 60, needle hub 32) are visible can be frosted (i.e. made opaque), to minimize the visual impact of the presence of the retraction mechanism as compared with the appearance of a traditional syringe.

Figure 23:
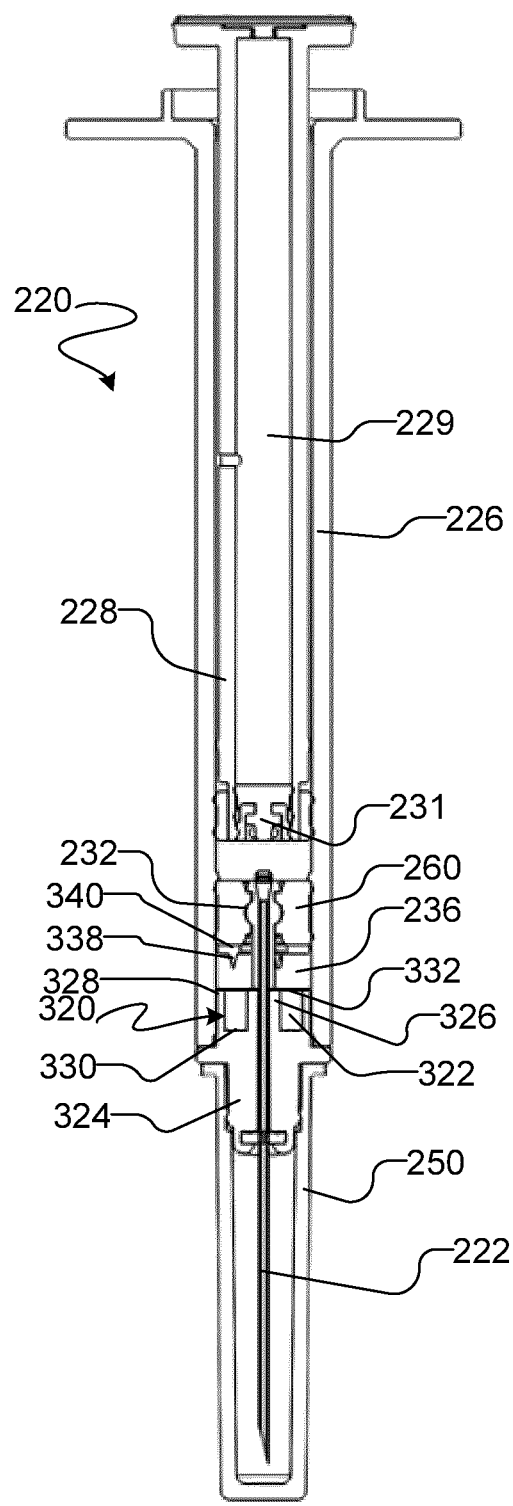
FIG. 23 is a cross-sectional view of an example embodiment of a retractable needle syringe having a unitary propellant release structure.

In some embodiments, as illustrated in FIG. 23, rather than providing propellant in a gas release cell such as gas release cell 34, propellant is contained within a unitary propellant release element that is integrally formed as a component of the gas actuated retractable syringe.

With reference to FIG. 23, an example embodiment of a retractable-needle syringe assembly 220 having a unitary propellant release element 320 is illustrated. Elements of retractable-needle syringe assembly 220 that are equivalent to elements of retractable-needle syringe assembly 20 described above are illustrated with reference numerals that have been incremented by 200, including retraction lumen 229, locking tip 231 and cap 250, and are not described again. In the illustrated embodiment, unitary propellant release element 320 is formed as a generally cylindrical channel 322 defined within a needle guide 324 of retractable-needle syringe assembly 220. Cylindrical channel 322 is defined by an inside cylindrical wall 326, an outside cylindrical wall 328, and a base 330 provided in needle guide 324.

Propellant is sealed within unitary propellant release element 320 by a seal 332, which extends over cylindrical channel 322 at the proximal end thereof. In the illustrated embodiment, seal 332 is sealingly engaged with upper proximal edges (shown as 334A/334B and 336A/336B in FIGS. 24A and 24B, and collectively referred to as upper edges 334 and 336) of inside wall 326 and outside wall 328, respectively. Seal 332 can be secured to upper proximal edges 334, 336 in any suitable manner, for example by heat sealing, ultrasonic welding, the use of suitable adhesives, or the like.

Seal 332 is positioned and configured so that it can be ruptured by rupturing members 338 upon the application of a post-injection force by a user. In the embodiment illustrated in FIG. 23, the relative orientation of the unitary propellant release element 320 and rupturing members 338 has been reversed relative to the orientation of gas release cell 34 and rupturing mechanism 38 described above. Additionally, the central neck of needle guide 324 (provided by inside cylindrical wall 326) is relatively shorter than the central neck 84 of needle guide 80, and the distal portion of the needle hub 232 is correspondingly elongated, to facilitate the positioning of unitary propellant release element 320 within needle guide 324. Needle guide 324 does not have an elongate central neck equivalent to central neck 84 of needle guide 80 so that seal 332 can be applied directly over both inside cylindrical wall 326 and outside cylindrical wall 328 during manufacture to seal propellant within channel 322.

Figure 24A:
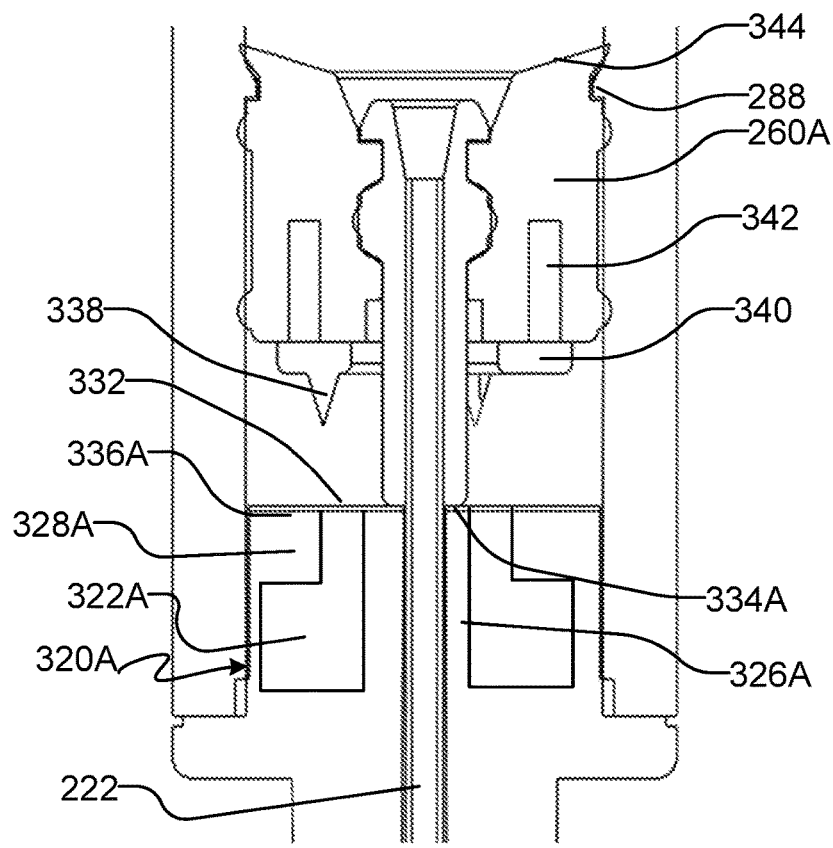
FIGS. 24A and 24B are cross-sectional views of different channel structures that can be used to provide a unitary propellant release structure.
Figure 24B:
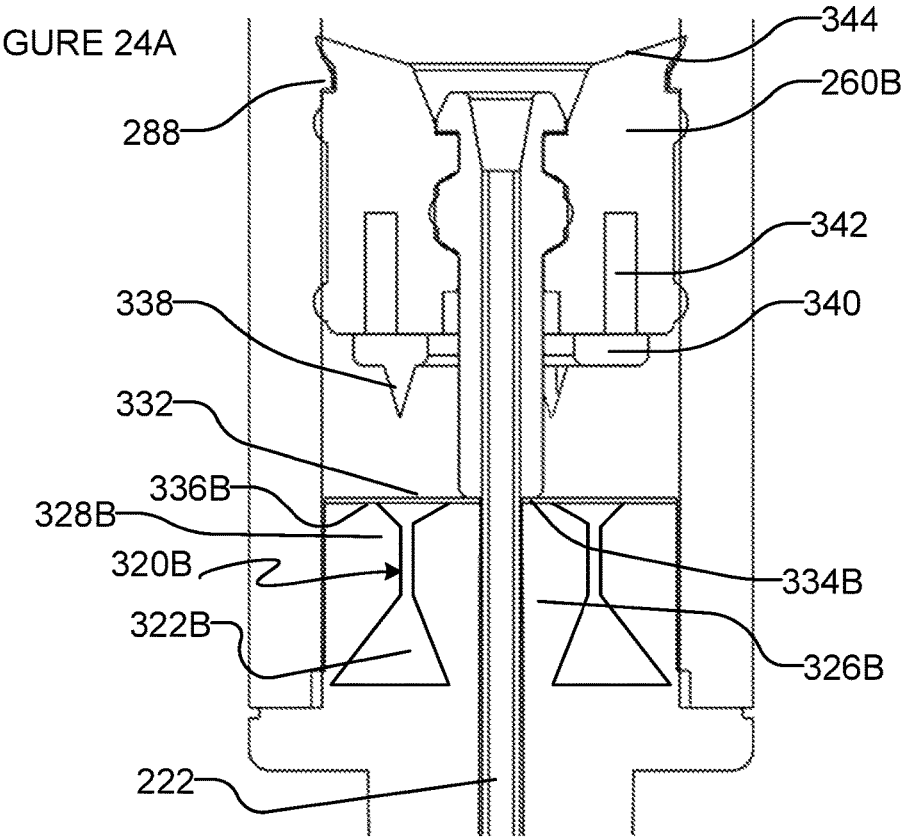
Figure 25:
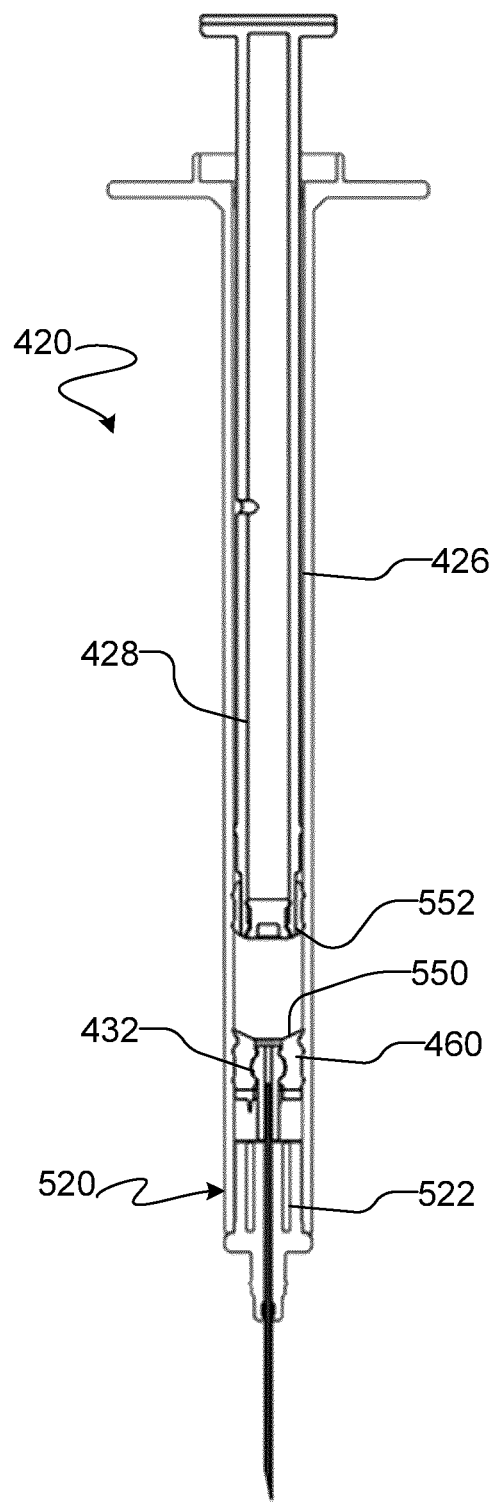
FIG. 25 is a sectional view of a further example embodiment of a retractable-needle syringe assembly having a unitary propellant release element.
Figure 26:
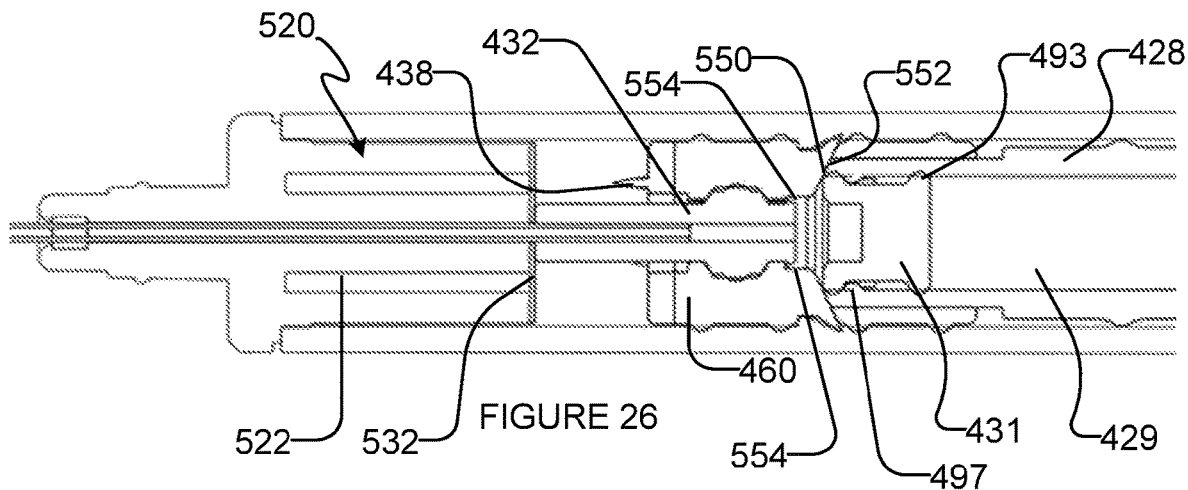
FIG. 26 is an enlarged sectional view of the embodiment illustrated in FIG. 25 just prior to actuation of the retraction mechanism, at the end of an injection stroke.
Figure 27:
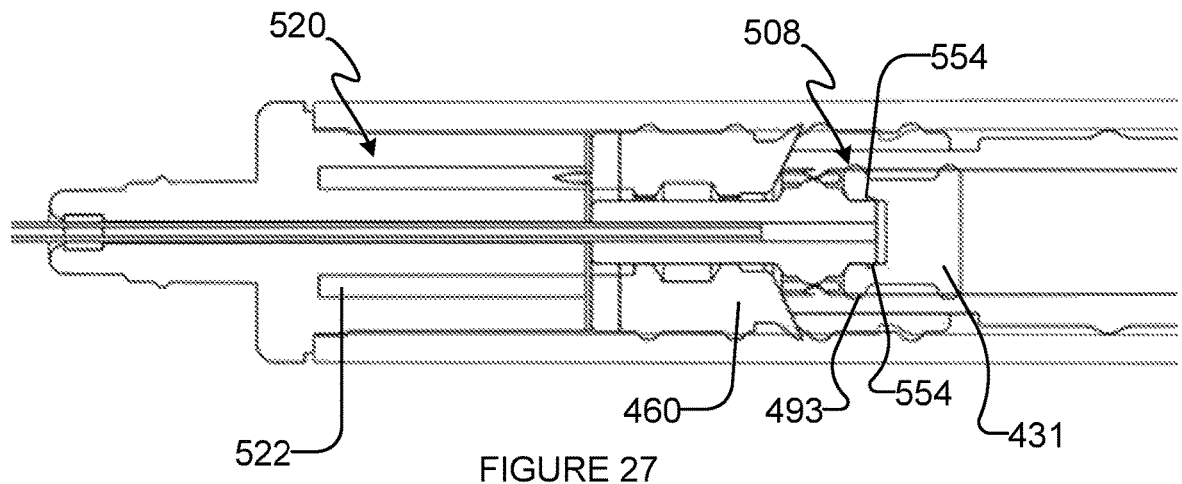
FIG. 27 is an enlarged sectional view of the embodiment illustrated in FIG. 25 just after actuation of the retraction mechanism by the application of a post-injection force by a user, before the needle retraction assembly starts to retract.
Figure 28:
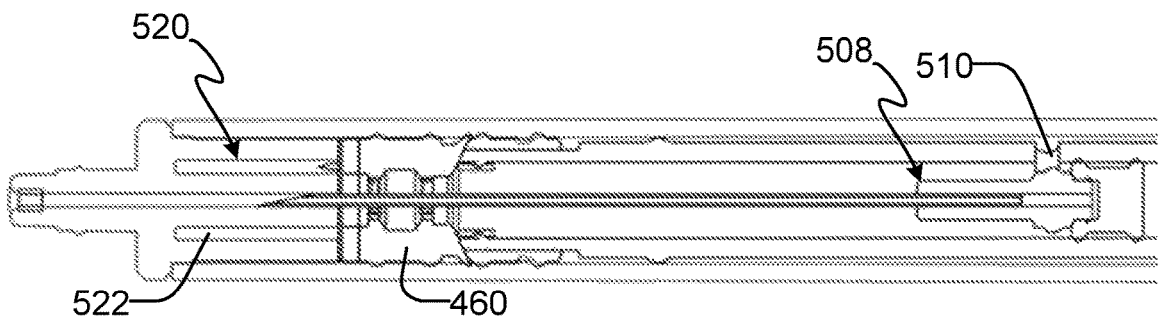
FIG. 28 is an enlarged sectional view of the embodiment illustrated in FIG. 25, showing the needle in the retracted position.

Rupturing members 338 are positioned proximally of unitary propellant release element 320 (rather than distally, as is the case for the position of rupturing mechanism 38 relative to gas release cell 34). Rupturing members 338 project in the distal direction, and are positioned to rupture seal 332 upon the application of a post-injection force by a user. In some example embodiments, including the illustrated embodiment, distally projecting rupturing members 338 are integrally formed with a disc-like base 340 as a rigid substrate, and false wall 260 is formed as an elastomeric overmold of this rigid substrate. In some embodiments, e.g. as shown in FIGS. 24A and 24B, disc-like base 340 is provided with a proximally projecting cylindrical extension 342, which assists in forming false wall 260 as an overmold of disc-like base 340. In some embodiments, apertures (not shown) are provided through proximally projecting cylindrical extension 342. Cylindrical extension 342, including any apertures therethrough, helps to provide a mechanical interference to lock the overmolded false wall 260 to disc-like base 340. In alternative embodiments, proximally projecting cylindrical extension 342 could be provided as one or more discrete projections, rather than being a fully revolved cylindrical feature. In further alternative embodiments, disc-like base 34 and false wall 260 are formed as separate components and joined together in any suitable manner (e.g. suitable adhesives).

In alternative embodiments, any suitable method can be used to manufacture rupturing members 338 and false wall 260 without including disc-like base 340, and these components can be joined together in any suitable manner, for example, using adhesives, suitable fasteners, or the like. In alternative embodiments, rupturing members 338 and false wall 260 are not joined together; for example, false wall 260 and disc-like base 340 bearing rupturing members 338 are pressed inside the interior surface of gas release chamber 236 with a friction fit to secure these elements in place.

Movement of false wall 260 in the distal direction thus also causes rupturing members 338 to move in the distal direction. Rupturing members 338 are oriented so that continued movement in the distal direction results in the rupture of seal 332, thereby releasing propellant from unitary propellant release element 320 into gas release chamber 236 of retractable-needle syringe assembly 220 so that needle retraction assembly 308 can be retracted in the manner described above for needle retraction assembly 108. In some embodiments, rupturing members 338 are provided with lateral indentations similar to lateral indentations 39, to ensure that there is a fluid path through which propellant can flow after seal 332 has been ruptured.

A sufficient amount of propellant is provided within unitary propellant release element 320 so that needle 222 is retracted a distance sufficient that the tip 252 of needle 222 sits fully within syringe barrel 226 after retraction, so that syringe assembly 220 no longer presents a sharps hazard after needle 222 has been retracted.

As with needle guide 80, needle guide 324 is fixed at the distal end of syringe barrel 226, and in the illustrated embodiment covers and sealingly engages the distal tip of syringe barrel 226. Needle guide 324 can be sealingly engaged with the distal end of syringe barrel 226 in any suitable manner, for example by suitably tight friction fit, the use of suitable adhesives, ultrasonic welding, compression fit using internal snap-type features to prevent removal of needle guide 324, or the like. While in the illustrated embodiment, needle guide 324 has been illustrated as being a separate piece from syringe barrel 226 that is coupled to syringe barrel 226, in alternative embodiments, needle guide 324 and syringe barrel 226 could be integrally formed. In some embodiments, providing needle guide 324 as a separate component facilitates the application of seal 332 over channel 322.

While unitary propellant release element 320 has been described above as having a generally cylindrical channel 322 formed in needle guide 324 and covered by a seal 332, it will be apparent to those skilled in the art that other configurations could be used to achieve the same function. Channel 322 can be provided with any desired shape, symmetrical or asymmetrical, so long as channel 322 can be sealed using a seal 332 to contain a propellant and allow seal 332 to be ruptured in response to the application of a post-injection force by a user. For example, with reference to FIGS. 24A and 24B, any suitable shape could be used in place of channel 322, and example embodiments in which channel 332 has been provided with irregular shapes are possible.

In the enlarged view of an example embodiment of a unitary propellant release element 320A illustrated in FIG. 24A, channel 322A has been provided with a relatively wide lower portion and a narrower upper portion. Channel 322A is provided with sufficient volume to hold a sufficient amount of propellant to be able to perform retraction of needle 222, and channel 322A is still positioned and configured to allow rupturing members 338 to rupture seal 332 and release propellant from unitary propellant release element 320A. Upper proximal edge 334A of inside wall 326A and upper proximal edge 336A of outside wall 328A are still provided, so that seal 332 can be sealingly secured in place over channel 322A to contain propellant within unitary propellant release element 320A.

Similarly, in the example embodiment of a unitary propellant release element 320B illustrated in FIG. 24B, channel 322B has been provided with a different shape, having a generally triangular upper portion and a generally triangular lower portion connected by a connecting passageway. Again, channel 322B is provided with sufficient volume to hold a sufficient amount of propellant to be able to perform retraction of needle 222, and channel 322B is still positioned and configured to allow rupturing members 338 to rupture seal 332 and release propellant from unitary propellant release element 320B. Upper proximal edge 334B of inside wall 326B and upper proximal edge 336B of outside wall 328B are still provided, so that seal 332 can be sealingly secured in place over channel 322B to contain propellant within unitary propellant release element 320B.

In alternative embodiments, rather than integrally forming generally cylindrical channel 322 within needle guide 324, generally cylindrical channel 322 could be formed by overmolding the inside and outside cylindrical walls 326, 328 over the proximal end of the needle guide, and then filling the resulting channel with propellant and sealing the propellant within the channel using a seal 332. In alternative embodiments, channel 322 could be discontinuous, e.g. provided as discrete pockets or chambers (i.e. channel 322 need not necessarily be a continuous cylindrical shape).

In some embodiments, a retractable-needle syringe having a unitary propellant release structure such as 320 is preferable to providing a syringe having a separate propellant release cell such as gas release cell 34 because it simplifies manufacture and assembly of the retractable needle syringe.

The operation and retraction of retractable-needle syringe assembly 220 is essentially as described above for retractable needle syringe assembly 20, except that on the application of a post-injection force by a user, movement of false wall 260 in the distal direction moves rupturing members 338 in the distal direction, towards the seal 332 of unitary propellant release element 320 (i.e. rather than movement of false wall 60 moving propellant release chamber 34 towards rupturing mechanism 38).

In the embodiment illustrated in FIGS. 24A and 24B, false wall 260A/260B has been modified as compared with false wall 260 shown in FIG. 23. In the embodiment of FIGS. 24A and 24B, false wall 260A/260B includes an angled proximal edge 344 that is angled distally in the inward direction from its outer edges. Although not shown, the tip of the plunger 228 that would be used with such an embodiment would be provided with a correspondingly tapered surface, as shown at 552 on the embodiment illustrated in FIGS. 25-28. In some embodiments, provision of angled proximal edge 344 is beneficial to cover false wall retention feature 288 in the proximal direction, because it has been found in some tested embodiments that where the false wall retention feature is provided as a plurality of discrete projections, air may be trapped between these projections, which may make it more difficult to purge air from the syringe.

An alternative embodiment of a retractable-needle syringe 420 having a unitary propellant release element is illustrated in FIGS. 25-28, in which reference numerals referring to elements that are the same as in retractable-needle syringe assembly 220 have been incremented by 200 (or incremented by 400 relative to like elements of syringe assembly 20), including barrel 426 and puncture lances 438. Retractable-needle syringe 420 differs from retractable-needle syringe 220 in having a narrower diameter, and also in having a different mechanism for coupling the plunger tip to the needle header to effect retraction of the needle. In some embodiments, the engagement mechanism for coupling the plunger tip to the needle header used in retractable-needle syringe 420 is more suited to use with a syringe assembly having a relatively narrower diameter. However, in alternative embodiments, the engagement mechanism described for retractable-needle syringe 420 could be used in syringes having a relatively wider diameter.

In the embodiment illustrated in FIGS. 25-28, unitary propellant release element 520 has a structure similar to unitary propellant release element 320, although channel 522 is slightly deeper because of the narrower diameter of retractable-needle syringe 420. The shape of false wall 460 is also modified as compared with syringe assemblies 20 and 220, and is similar to the embodiments illustrated in FIGS. 24A and 24B, in that the proximal edge 550 of false wall 460 is tapered inwardly in the distal direction from its outer edge. The tip of plunger 428 includes a correspondingly angled surface 552 that contacts proximal edge 550 when plunger 428 reaches the end of its injection stroke. The plunger 428 includes a vent 510.

Needle hub 432 is generally similar to needle hub 232 and 32, except that the proximal portion thereof is modified as described below to engage with locking tip 431 in a manner different from the way that needle hub 32 and locking tip 31 engage. The function of locking tip 431 is somewhat similar to locking tip 31, but again the distal portion thereof is modified as described below. Additionally, because barbs 554 are provided on needle hub 432, locking tip 431 is formed as a single component made from a material into which barbs 554 can engage or bite (e.g. from silicone, an elastomer, or other similar polymer), rather than being formed as two components, one relatively rigid and one more flexible, as is the case for locking tip 31. The material from which needle hub 432 is made should be more rigid than the material from which locking tip 431 is made, to facilitate barbs 554 engaging with locking tip 431 as aforesaid.

In particular, the distal end of needle hub 432 is provided with one or more barbs 554. In the illustrated embodiment, barbs 554 project radially outwardly and in a distal direction from the central axis of needle hub 432. Needle hub 432 does not have a generally cylindrical locking element with a locking edge like locking edge 58 of needle hub 32. In some embodiments, barbs 554 are provided as a fully revolved feature extending fully around the outer perimeter of the proximal portion of needle hub 432. In some embodiments, barbs 554 are provided as one or a plurality of discrete features around the outer perimeter of the proximal portion of needle hub 432. It will be clear to those skilled in the art that positioning of barbs 554 at the proximal end of needle hub 432 and the exact configuration of barbs 554 is not essential, as long as barbs 554 are positioned on needle hub 432 so that they can engage with locking tip 431 as described below.

Barbs 554 are positioned and configured so that when locking tip 431 is forced over the proximal portion of needle hub 432 by the application of a post-injection force, barbs 554 bite into the relatively softer material from which locking tip 431 is formed, thereby securing locking tip 431 and needle hub 432 to provide a needle retraction assembly 508. The engagement between the proximal portion of needle hub 432 and the relatively softer material of locking tip 431 provides a sufficient seal to allow for needle retraction and to prevent the further flow of medicament through the needle.

Because needle hub 432 is provided with barbs 554, the distal portion of locking tip 431 does not have special structural features on its inside surface (e.g. similar to locking aperture 92 or central cylindrical projection 89) for engagement with needle hub 432. Locking tip 431 is just formed so that barbs 554 can engage with the interior surface thereof. The features on the outer edges of locking tip 431 that sealingly engage with the interior of retraction lumen 429, including sealing rings 493, are the same as described for locking tip 31.

To secure locking tip 431 within the distal tip of plunger 428, in some embodiments, including the illustrated embodiment, one of the sealing rings 493 is initially positioned distally of capture projections 497, to prevent movement of locking tip 431 in the proximal direction during the application of a loading force or an injection force, but this engagement is broken by the release of propellant from unitary propellant release element 520 so that locking tip 431 (and therefore needle retraction assembly 508) can be retracted within retraction lumen 429. Additionally or alternatively, because air is expelled between the locking tip 431 and the interior surface of plunger 428 during insertion of locking tip 431, a vacuum lock is formed that holds locking tip 431 in place against forces experienced during application of a loading force and an injection force on syringe assembly 420. Thus, in some embodiments capture projections 497 are omitted and only a vacuum lock is used to secure locking tip 431 within the distal tip of plunger 428. The force required to engage barbs 554 with locking tip 431 should be less than the force required to disengage the engagement of sealing ring 493 and capture projections 497 and displace the vacuum seal securing locking tip 431 in place, to facilitate reliable needle retraction.

Lateral indentations (not shown, but similar to lateral indentations 39) on rupturing mechanism 538 are provided in some embodiments to ensure that there is a fluid path through which propellant can flow after seal 532 has been ruptured.

The operation of retractable-needle syringe assembly 420 is generally as described for syringe assemblies 20 and 220, except that the sealing engagement between the locking tip 431 and needle hub 432 is provided by the engagement of barbs 554 with the relatively softer material of locking tip 431 upon the application of a post-injection force by a user.

While a number of exemplary aspects and embodiments have been discussed above, those of skill in the art will recognize certain modifications, permutations, additions and sub-combinations thereof. Accordingly, the scope of the claims should not be limited by the preferred embodiments set forth in the description, but should be given the broadest interpretation consistent with the specification as a whole.

What is claimed is:

1. A retractable-needle syringe comprising:
   a syringe barrel;
   a plunger slidably disposed within and sealingly engaged with the syringe barrel, the plunger having a retraction lumen defined therein for receiving a needle when the retractable-needle syringe is actuated;
   the needle coupled to a distal end of the syringe barrel and in fluid communication with a medicament chamber defined within the syringe barrel distally of the plunger;
   a needle hub for securing the needle at the distal end of the syringe barrel, the needle hub being initially secured within a false wall against a loading force or an injection force applied by a user, and releaseable from the false wall in response to a post-injection force applied by the user;
   a locking tip provided at a distal end of the plunger, the locking tip being in sealing engagement with and initially secured within the retraction lumen against the loading force or the injection force applied by the user, and releasable for sliding retraction within the retraction lumen in response to release of propellant upon the post-injection force applied by the user, the locking tip being engageable with the needle hub in response to the post-injection force to provide a retraction assembly comprising the locking tip, the needle hub, and the needle;
   a propellant release cell positioned distally of the needle hub and containing the propellant; and
   a rupture mechanism positioned to puncture the propellant release cell in response to application of the post-injection force by the user to thereby drive retraction of the retraction assembly within the retraction lumen,
   wherein the needle hub comprises a tapered sealing portion on an inner surface of the needle hub at a proximal portion of the needle hub, a proximal end of the tapered sealing surface being wider than a width of the tapered sealing surface at any point distal to the proximal end of the tapered sealing surface, and wherein the locking tip of the plunger comprises a central projection with a tapered surface that is complementary to the tapered sealing portion of the needle hub, so that the tapered sealing portion and the tapered surface can be brought together into sealing contact upon the application of the post-injection force; and
   wherein the false wall comprises a central aperture extending axially therethrough, and a radially-outwardly projecting channel defined circumferentially on an interior portion of the central aperture, and wherein the needle hub comprises radially outwardly projecting engagement features for initially sealingly engaging with the channel, the engagement features being displaceable from the channel in response to the application of the post-injection force by the user.

2. The retractable-needle syringe as defined in claim 1, wherein the needle hub comprises barbs near a proximal portion of the needle hub, and wherein the locking tip comprises a relatively softer material than the barbs, so that the barbs can be engaged with the locking tip upon the application of the post-injection force by the user to provide the retraction assembly.

3. The retractable-needle syringe as defined in claim 2, wherein the locking tip is initially secured within the retraction lumen by a vacuum lock.

4. The retractable-needle syringe as defined in claim 1, wherein the needle hub comprises a locking element at a proximal end of the needle hub, and wherein the locking tip of the plunger comprises at least one plunger locking edge for engaging with the locking element in a snap-fit engagement, wherein a proximal end of the locking element comprises a tapered portion that is tapered radially outwardly with a generally radially extending needle hub locking edge provided at the outside distal edge of the tapered portion, so that the plunger locking edge can slide over the tapered portion in the distal direction and engage with the needle hub locking edge.

5. The retractable-needle syringe as defined in claim 4, wherein the locking tip comprises an overmold of a flexible component on a rigid component, and wherein the plunger locking edge is provided on the rigid component and the central projection of the locking tip is provided on the flexible component.

6. The retractable-needle syringe as defined in claim 5, wherein the locking tip comprises two axially aligned sealing rings provided on an outside circumference of the locking tips for sealing engagement with the retraction lumen, wherein the sealing rings are provided on the flexible component of the overmolded locking tip.

7. The retractable-needle syringe as defined in claim 1, wherein one or more radially inwardly extending capture projections are provided distally within the retraction lumen of the plunger, and wherein the plunger tip comprises one or more distal grooves for initially engaging the locking tip with the capture projections, the engagement between the distal groove and the capture projections being sufficiently strong to withstand the application of the loading force or the injection force but releasable in response to the post-injection force applied by the user.

8. The retractable-needle syringe as defined in claim 1, wherein an axially inwardly projecting support projection is provided within the central aperture at a distal end of the channel.

9. The retractable-needle syringe as defined in claim 1, wherein a surface of a central aperture of the false wall is provided with surface features that prevent formation of an airtight seal between the false wall and the needle hub after the needle hub has been released from the false wall by the application of the post-injection force by the user, wherein the surface features comprise vent channels extending axially along the axially inwardly projecting support projections.

10. The retractable-needle syringe as defined in claim 1, wherein an interior surface of the syringe barrel comprises a radially-inwardly extending false wall retention feature for defining a position of axial insertion of the false wall within the syringe during assembly, wherein the false wall retention feature optionally has a proximal angled portion that slopes radially outwardly from an inside edge of the false wall retention feature in the proximal direction.

11. The retractable-needle syringe as defined in claim 10, wherein the false wall retention feature comprises one or more discrete projections.

12. The retractable-needle syringe as defined in claim 11, wherein the false wall retention features comprise four discrete projections spaced apart by approximately 90°.

13. The retractable-needle syringe as defined in claim 1, comprising a vent hole through the plunger, wherein the vent hole is axially positioned within the retraction lumen just distal of the fully retracted position of the locking tip.

14. The retractable-needle syringe as defined in claim 1, comprising grooves formed on an inside surface of the retraction lumen for venting excess propellant after needle retraction, wherein the grooves extend axially from a point in the retraction lumen just distal of the fully retracted position of the locking tip to a proximal portion of the retraction lumen.

15. The retractable-needle syringe as defined in claim 14, comprising vents through a proximal plunger end flange of the plunger, to allow propellant to flow through the grooves even after the plunger approaches its distal limit of travel.

16. The retractable-needle syringe as defined in claim 1, comprising an anti-tamper ring provided at a proximal end of the syringe, the anti-tamper ring comprising a ring having a shape complementary to a proximal end of the plunger, the anti-tamper ring extending proximally from the syringe to generally surround the proximal end of the plunger to prevent the insertion of tools between the end of the plunger and the syringe.

17. The retractable-needle syringe as defined in claim 1, wherein the rupture mechanism comprises at least one puncture lance, and wherein the puncture lance comprises at least one lateral indentation to provide a flow path for propellant during rupture of the propellant release cell or the unitary propellant release structure.

18. The retractable-needle syringe as defined in claim 1, comprising at least one vent hole provided through a proximal end of the plunger, to allow air to be forced out of the retraction lumen as the needle is retracted, wherein a proximal end of the plunger comprises surface features for preventing occlusion of the at least one vent hole, and wherein the surface features comprise a series of axially extending thumb ridges.

19. A retractable-needle syringe comprising:
a barrel;
a plunger axially slideable within the barrel for drawing medicament into a medicament chamber defined within the barrel and for injecting medicament into a patient, the plunger having a retraction lumen therein;
a locking tip engaged at a distal end of the plunger within the retraction lumen, the locking tip being initially secured against a loading force or an injection force applied by a user, but moveable in response to application of a post-injection force by the user to allow sliding retraction of the locking tip within the retraction lumen;
a false wall initially engaged within the barrel near a distal end of the barrel, the false wall being moveable in a distal direction in response to the application of the post-injection force by the user;
a needle hub initially secured by the false wall against the loading force or the injection force applied by the user, the needle hub being engageable with the locking tip to provide a retraction assembly comprising the locking tip, the needle hub, and a needle, and the needle hub being releaseable from the false wall, upon the application of the post-injection force by the user;
the needle projecting from the distal end of the barrel, the needle being secured to the needle hub;
a unitary propellant release structure provided distally of the needle hub within the barrel, wherein the unitary propellant release structure comprises a channel defined within a distal portion of the barrel, the channel comprising a base, an inner wall and an outer wall, with a seal extending between upper edges of the inner and outer walls to contain a propellant within the unitary propellant release structure; and
a rupturing member moveable to rupture the unitary propellant release structure upon the application of the post-injection force by the user to thereby drive retraction of the retraction assembly into the retraction lumen,
wherein the needle hub comprises a tapered sealing portion on an inner surface of the needle hub at a proximal portion of the needle hub, a proximal end of the tapered sealing surface being wider than a width of the tapered sealing surface at any point distal to the proximal end of the tapered sealing surface, and wherein the locking tip of the plunger comprises a central projection with a tapered surface that is complementary to the tapered sealing portion of the needle hub, so that the tapered sealing portion and the tapered surface can be brought together into sealing contact upon the application of the post-injection force; and
wherein the false wall comprises a central aperture extending axially therethrough, and a radially-outwardly projecting channel defined circumferentially on an interior portion of the central aperture, and wherein the needle hub comprises radially outwardly projecting engagement features for initially sealingly engaging with the channel, the engagement features being displaceable from the channel in response to the application of the post-injection force by the user.

* * * * *